(12) United States Patent
Saadat et al.

(10) Patent No.: US 11,576,559 B2
(45) Date of Patent: Feb. 14, 2023

(54) DIRECT VISION CRYOSURGICAL PROBE AND METHODS OF USE

(71) Applicant: Arrinex, Inc., Redwood City, CA (US)

(72) Inventors: Vahid Saadat, Atherton, CA (US); Matthew Herron, Menlo Park, CA (US); Richard C. Ewers, Fullerton, CA (US)

(73) Assignee: Arrinex, Inc., Redwood City, CA (US)

( * ) Notice: Subject to any disclaimer, the term of this patent is extended or adjusted under 35 U.S.C. 154(b) by 240 days.

(21) Appl. No.: 17/030,047

(22) Filed: Sep. 23, 2020

(65) Prior Publication Data

US 2021/0000331 A1 Jan. 7, 2021

Related U.S. Application Data

(63) Continuation of application No. 15/804,652, filed on Nov. 6, 2017, now Pat. No. 10,813,533, which is a
(Continued)

(51) Int. Cl.

| A61B 1/00 | (2006.01) |
|---|---|
| A61B 18/02 | (2006.01) |
| A61B 1/018 | (2006.01) |
| A61B 1/05 | (2006.01) |
| A61B 1/06 | (2006.01) |

(Continued)

(52) U.S. Cl.
CPC ...... *A61B 1/00082* (2013.01); *A61B 1/00087* (2013.01); *A61B 1/00177* (2013.01); *A61B 1/00179* (2013.01); *A61B 1/00183* (2013.01); *A61B 1/018* (2013.01); *A61B 1/05* (2013.01); *A61B 1/0615* (2013.01); *A61B 1/0623* (2013.01); *A61B 1/233* (2013.01); *A61B 18/02* (2013.01); *A61B 2018/00577* (2013.01); *A61B 2018/00982* (2013.01);

(Continued)

(58) Field of Classification Search
CPC ................ A61B 1/00082; A61B 18/02; A61B 2018/00982; A61B 2018/00577
See application file for complete search history.

(56) References Cited

U.S. PATENT DOCUMENTS

| 5,409,483 A * | 4/1995 | Campbell | ............ A61N 5/0601 606/15 |
|---|---|---|---|
| 6,979,290 B2 * | 12/2005 | Mourlas | ............. A61B 1/00082 600/116 |

(Continued)

*Primary Examiner* — Matthew J Kasztejna
(74) *Attorney, Agent, or Firm* — McDonnell Boehnen Hulbert & Berghoff LLP

(57) ABSTRACT

A direct vision cryosurgical and methods of use are described herein where the device may generally comprise an elongated rigid structure with a distal end, a proximal end, and a central lumen. The distal end may comprise a non-coring optically transparent needle tip with at least one lateral fenestration in communication with the central lumen. The distal end may also house at least one imaging device configured for distal imaging. A proximal end of the device may comprise a handle with a means for connecting the imaging device(s) to an imaging display(s), and a means for accessing bodily tissue in the vicinity of the distal end with a cryo-ablation probe through the central lumen and the lateral fenestration(s) for diagnostic or therapeutic purposes.

19 Claims, 19 Drawing Sheets

Section B - B

Related U.S. Application Data continuation of application No. 14/339,024, filed on Jul. 23, 2014, now abandoned.

(60) Provisional application No. 61/858,104, filed on Jul. 24, 2013.

(51) Int. Cl.
    *A61B 1/233*     (2006.01)
    *A61B 18/00*     (2006.01)

(52) U.S. Cl.
    CPC ............... *A61B 2018/0212* (2013.01); *A61B 2018/0262* (2013.01); *A61B 2018/0293* (2013.01)

(56) References Cited

U.S. PATENT DOCUMENTS

| | | | |
|---|---|---|---|
| 7,022,120 B2* | 4/2006 | Lafontaine | C22B 23/021 606/20 |
| 8,235,976 B2* | 8/2012 | Lafontaine | A61B 18/02 606/20 |
| 2008/0021271 A1* | 1/2008 | Pasero | A61B 1/00039 600/109 |
| 2008/0275445 A1* | 11/2008 | Kelly | A61B 18/18 606/45 |
| 2008/0312644 A1* | 12/2008 | Fourkas | A61B 18/02 606/22 |
| 2010/0125266 A1* | 5/2010 | Deem | A61B 17/320036 606/192 |
| 2012/0143177 A1* | 6/2012 | Avitall | A61B 18/1492 606/41 |
| 2012/0209261 A1* | 8/2012 | Mayse | A61B 18/18 606/41 |
| 2013/0018367 A1* | 1/2013 | Wu | A61B 18/0218 606/21 |
| 2013/0184532 A1* | 7/2013 | Goldfarb | A61B 1/00066 600/171 |
| 2015/0080870 A1* | 3/2015 | Wittenberger | A61M 25/0147 606/23 |
| 2015/0196345 A1* | 7/2015 | Newell | A61B 18/02 606/21 |

* cited by examiner

Section A - A

Section B - B

Section C - C

Section D - D

DIRECT VISION CRYOSURGICAL PROBE AND METHODS OF USE

CROSS-REFERENCE TO RELATED APPLICATIONS

The present application is a Continuation of U.S. application Ser. No. 15/804,652, filed Nov. 6, 2017, which is a Continuation of U.S. application Ser. No. 14/339,024 filed Jul. 23, 2014, which claims priority to U.S. Provisional Application Ser. No. 61/858,104 filed Jul. 24, 2013, the full disclosures of these applications being incorporated herein by reference in their entirety for all purposes.

FIELD OF THE INVENTION

The present invention relates to cryosurgical probes and their methods of use. More particularly, the present invention relates to cryosurgical probes which are configured to be advanced into a body lumen while providing for direct visualization.

BACKGROUND OF THE INVENTION

Accessing and treating regions within a body lumen such as the nasal cavities are often performed by utilizing a probe which is cooled via a chilled fluid, a cryo-fluid such as Nitrous Oxide, or through some other cooling mechanism. The cooled tip can be placed into contact against the tissue region to be treated. However, proper positioning of the cooling probe relative to the tissue may be difficult to achieve due to a number of factors such as limited space, lack of visual contact, anatomical obstructions, etc.

Accordingly, devices and methods which can overcome such obstacles to effectively treat tissue regions in body lumens through cryo-therapy are needed.

SUMMARY OF THE INVENTION

It is an object of this invention to provide a surgical system for image guided cryo-ablation of a discrete anatomical structure within a mammalian body, through a surgically created or natural body orifice, for the purpose of diagnosing or treating disease or injury.

In accordance with one aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-ablation probe through the central lumen and the lateral fenestration(s) for diagnostic or therapeutic purposes.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-surgical probe through the central lumen and the lateral fenestration(s) for diagnostic or therapeutic purposes, whereby the needle tip is configured for advancement towards a surgical target through a facial boundary between two or more discrete anatomical structures in a substantially atraumatic manner, and the imaging device is used to guide the advancement of the needle tip.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging, and further comprising an inflatable structure proximal to the needle tip; said proximal end comprising a handle with a means for connecting the imaging device(s) to an imaging display(s), and a means for accessing bodily tissue in the vicinity of the distal end with a cryosurgical probe through the central lumen and the lateral fenestration(s) for diagnostic or therapeutic purposes, and a means for inflating the inflatable structure, whereby the needle tip is configured for advancement towards a surgical target through a facial boundary between two or more discrete anatomical structures in a substantially atraumatic manner, and the imaging device is used to guide the advancement of the needle tip, and the inflatable structure is configured to further separate the anatomical structure(s) as the needle tip is advanced.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the objective lens, a CMOS imaging sensor, and at least one light emitting diode configured for tissue illumination.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-surgical probe through the central lumen and the lateral fenestration(s) for diagnostic or therapeutic purposes, whereby the imaging device is an endoscope comprising an objective lens, a coherent fiber optic bundle configured for imaging, and a second optical bundle configured for illumination.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-surgical probe through the central lumen and the lateral fenestration(s) for diagnostic or therapeutic purposes, whereby the imaging device is an endoscope comprising an objective lens, and at least one relay lens configured for tissue imaging, and a fiber optic bundle configured for tissue illumination.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-surgical probe through the central lumen and the lateral fenestration(s) for diagnostic or therapeutic purposes, whereby the minor dimension of the lateral fenestration approximates the working diameter of the central lumen.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end with a cryo-surgical probe through the central lumen and the lateral fenestration(s) for diagnostic or therapeutic purposes, whereby the lateral fenestration is substantially perpendicular to the axis of the central lumen.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging, and at least one cryo-surgical probe configured for distal tissue freezing; said proximal end comprising a handle with a means for connecting the imaging device(s) to an imaging through the central lumen and the lateral fenestration(s) for diagnostic or therapeutic purposes, whereby the fluid is a clear ionic liquid.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging, and at least one cryo-surgical probe configured for distal tissue freezing; said proximal end comprising a handle with a means for connecting the imaging device(s) to an imaging display(s), and a means for delivering or removing fluid to/from the vicinity of the distal end through the central lumen and the lateral fenestration(s) for diagnostic or therapeutic purposes, whereby the fluid is pressurized to facilitated dissection and distal advancement.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging, and at least one cryo-surgical probe configured for distal tissue freezing; said proximal end comprising a handle with a means for connecting the imaging device(s) to an imaging display(s), and a means for delivering or removing fluid from the vicinity of the distal end through the central lumen and the lateral fenestration(s) for diagnostic or therapeutic purposes, whereby the fluid is an evaporated liquid refrigerant that is introduced to the distal region by the cryosurgical probe during distal tissue freezing.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging, and at least one cryo-surgical probe configured for distal tissue freezing; said proximal end comprising a handle with a means for connecting the imaging device(s) to an imaging display(s), and a means for delivering or removing fluid to/from the vicinity of the distal end through the central lumen and the lateral fenestration(s) for diagnostic or therapeutic purposes, whereby the fluid is comprises an anesthetic.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end through the central lumen and the lateral fenestration(s) for diagnostic or therapeutic purposes, whereby the handle, central lumen, and lateral fenestration are configured to receive a surgical probe for surgical access to distal tissue, wherein the surgical probe may be a cryosurgical probe configured for distal tissue freezing.

In accordance with another aspect of this invention is a surgical device comprising an elongated rigid structure with a distal end, a proximal end, and a central lumen; with said distal end comprising a non-coring optically transparent needle tip with at least one lateral fenestration in device(s) to an imaging display(s), and a means for accessing bodily tissue in the vicinity of the distal end through the central lumen and the lateral fenestration(s) for diagnostic or therapeutic purposes, whereby the handle, central lumen, and lateral fenestration are configured to receive a surgical probe for surgical access to distal tissue, wherein the surgical probe may be a cryosurgical probe configured for distal tissue freezing by means of direct application of liquid refrigerant to the target distal tissue.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end through the central lumen and the lateral fenestration(s) for diagnostic or therapeutic purposes, whereby the handle, central lumen, and lateral fenestration are configured to receive a surgical probe for surgical access to distal tissue, wherein the surgical probe may be a cryosurgical probe configured for distal tissue freezing comprising a distal refrigerant evaporation chamber in direct contact with the target distal tissue, with the evaporation chamber comprising a hollow metallic structure.

In accordance with another aspect of this invention is a surgical device comprising an elongated rigid structure with a distal end, a proximal end, and a central lumen; with said distal end comprising a non-coring optically transparent needle tip with at least one lateral fenestration in communication with the central lumen, housing at least one imaging device configured for distal imaging; said proximal end comprising a handle with a means for connecting the imaging device(s) to an imaging display(s), and a means for accessing bodily tissue in the vicinity of the distal end through the central lumen and the lateral fenestration(s) for diagnostic or therapeutic purposes, whereby the handle, central lumen, and lateral fenestration are configured to receive a surgical probe for surgical access to distal tissue, wherein the surgical probe may be a cryosurgical probe configured for distal tissue freezing comprising a distal refrigerant evaporation chamber in direct contact with the target distal tissue, with the evaporation chamber comprising an inflatable balloon.

In accordance with another aspect of this invention is a method for accessing a distal region in a mammalian body through a natural dissection plane in order to perform at least one diagnostic or therapeutic cryosurgical step comprising inserting into the body a surgical device comprising an elongated rigid structure with a distal end, a proximal end, and a central lumen; with said distal end comprising a non-coring optically transparent needle tip with at least one lateral fenestration in communication with the central lumen, and housing at least one imaging device configured for distal imaging, and housing at least one removable cryosurgical probe configured for distal tissue freezing; said proximal end comprising a handle with a means for connecting the imaging device(s) to an imaging display(s), and a means for accessing bodily tissue in the vicinity of the distal end through the central lumen and the lateral fenestration(s); then advancing the surgical device in the direction of the distal region while maneuvering the distal tip between the facial boundaries of intervening anatomical structures using images from the imaging device(s) and imaging display(s) to guide the maneuvering.

In accordance with another aspect of this invention is a method for accessing a distal region in a mammalian body through a natural dissection plane in order to perform at least one diagnostic fenestration in communication with the central lumen, and housing at least one imaging device configured for distal imaging, and further comprising an inflatable structure proximal to the needle tip; said proximal end comprising a handle with a means for connecting the imaging device(s) to an imaging display(s), and a means for accessing bodily tissue in the vicinity of the distal end through the central lumen and the lateral fenestration(s) for diagnostic or therapeutic purposes, and a means for inflating the inflatable structure; then advancing the surgical device in the direction of the distal region while maneuvering the distal tip between the facial boundaries of intervening anatomical structures using images from the imaging device(s) and imaging display(s) to guide the maneuvering, and inflating the inflatable structure as needed to facilitate distal advancement.

In accordance with an alternative embodiment of this invention is a cryosurgical probe comprising an elongated structure with a distal end, a proximal end, and at least one central lumen; with said distal end comprising an inflatable balloon structure configured as a refrigerant evaporation chamber, and as an optical imaging window, enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas.

An alternative embodiment of this invention is a cryosurgical probe comprising an elongated structure with a distal end, a proximal end, and at least one central lumen; with said distal end comprising an inflatable balloon structure configured as a refrigerant evaporation chamber, and as an optical imaging window, enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas.

In accordance with one aspect of the alternative embodiment of this invention is a cryosurgical probe comprising an elongated structure with a distal end, a proximal end, and at least one central lumen; with said distal end comprising an inflatable balloon structure configured as a refrigerant evaporation chamber, and as an optical imaging window, enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby, the imaging device is configured for lateral imaging.

In accordance with another aspect of the alternative embodiment of this invention is a cryosurgical probe comprising an elongated structure with a distal end, a proximal end, and at least one central lumen; with said distal end comprising an inflatable balloon structure configured as a refrigerant evaporation chamber, and as an optical imaging window, enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby, the imaging device comprises at least one coherent optical fiber bundle, configured for transmitting an image from within the inflatable balloon to a camera in the vicinity of the proximal end.

In accordance with another aspect of the alternative embodiment of this invention is a cryosurgical probe comprising an elongated structure with a distal end, a proximal end, and at least one central lumen; with said distal end comprising an inflatable balloon structure configured as a refrigerant evaporation chamber, an optical imaging window, and as a tissue dilator enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby, the imaging device comprises a probe with a distal end and a proximal end configured for removable insertion into the inflatable balloon through a central lumen, with the distal end comprising an imaging means, and the proximal end comprising a means for connecting the probe to an image display.

In accordance with another aspect of the alternative embodiment of this invention is a cryosurgical probe comprising a substantially rigid elongated structure with a distal end, a proximal end, and at least one central lumen; with said distal end comprising an inflatable balloon structure configured as a refrigerant evaporation chamber, an optical imaging window, and as a tissue dilator enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby the cryosurgical probe is configured for insertion into the targeted surgical site.

In accordance with another aspect of the alternative embodiment of this invention is a cryosurgical probe comprising a substantially flexible elongated structure with a distal end, a proximal end, and at least one central lumen; with said distal end comprising an inflatable balloon structure configured as a refrigerant evaporation chamber, an optical imaging window, and as a tissue dilator enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby the cryosurgical probe is configured for insertion into the targeted surgical site by means of a tortuous insertion pathway.

In accordance with another aspect of the alternative embodiment of this invention is a cryosurgical probe comprising an elongated structure with a distal end, a proximal end, and at least one central lumen; with said distal end comprising an inflatable balloon structure configured as a refrigerant evaporation chamber, an optical imaging window, and as a tissue dilator enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas, whereby the predetermined pressure is maintained by a pressure relief valve in line between the interior of the balloon and the ambient atmosphere, wherein the cryosurgical probe is configured for lateral tissue freezing by means of spraying a liquid refrigerant at an interior radial segment of the balloon from a central lumen. cryosurgical probe comprising an elongated structure with a distal end, a proximal end, and at least one central lumen; with said distal end comprising an outer inflatable balloon structure configured as an optical imaging window, and as a tissue dilator enclosing at least one optical imaging device, at least one inner cryogenic evaporator balloon, and at least one inner thermal insulation balloon; with said proximal end comprising a means for introducing a liquid refrigerant into the cryogenic evaporator balloon through a central lumen, a means of removing evaporated refrigerant from the cryogenic evaporator balloon through a central lumen at a predetermined pressure, a means for inflating the thermal insulation balloon with the pressurized evaporated refrigerant gas, a means for connecting the optical imaging device(s) to an imaging display, and a means for inflating the outer balloon with a liquid or a gas.

In accordance with another aspect of the alternative embodiment of this invention is a cryosurgical probe comprising an elongated structure with a distal end, a proximal end, and at least one central lumen; with said distal end comprising an outer inflatable balloon structure configured as an optical imaging window, and as a tissue dilator enclosing at least one optical imaging device, at least one inner cryogenic evaporator balloon, and at least one inner thermal insulation balloon; with said proximal end comprising a means for introducing a liquid refrigerant into the cryogenic evaporator balloon through a central lumen, a means of removing evaporated refrigerant from the cryogenic evaporator balloon through a central lumen at a predetermined pressure, a means for inflating the thermal insulation balloon with the pressurized evaporated refrigerant gas, a means for connecting the optical imaging device(s) to an imaging display, and a means for inflating the outer balloon with a liquid or a gas, whereby the outer balloon is fabricated from a substantially non-elastic material, and the inner balloons are fabricated from a substantially elastic material.

In accordance with another aspect of the alternative embodiment of this invention is a cryosurgical probe comprising an elongated structure with a distal end, a proximal end, and at least one central lumen; with said distal end comprising an outer inflatable balloon structure configured as an optical imaging window, and as a tissue dilator enclosing at least one removably insertable optical imaging device, at least one inner cryogenic evaporator balloon, and at least one inner thermal insulation balloon; with said proximal end comprising a means for introducing a liquid refrigerant into the cryogenic evaporator balloon through a central lumen, a means of removing evaporated refrigerant from the cryogenic evaporator balloon through a central lumen at a predetermined pressure, a means for inflating the thermal insulation balloon with the pressurized evaporated refrigerant gas, a means for connecting the optical imaging device(s) to an imaging display, and a means for inflating the outer balloon with a liquid or a gas, whereby the inner balloons are configured to conform to the inner surface of the outer balloon when pressurized with refrigerant.

It is further an object of this invention to provide a method for performing a cryosurgical procedure comprising inserting a cryosurgical probe into the body of a patient, and then advancing the distal end of the probe into the vicinity of the surgical target, with the cryosurgical probe comprising: an elongated structure with a distal end, a proximal end, and at least one central lumen; with said distal end comprising an inflatable balloon structure configured as a refrigerant evaporation chamber, and as an optical imaging window enclosing at least one optical imaging device; with said proximal end comprising a means for introducing a liquid refrigerant into the distal balloon through a central lumen, a means of removing evaporated refrigerant from the cryosurgical probe at a predetermined pressure, a means for connecting the optical imaging device(s) to an imaging display, and a means for inflating the balloon with a liquid or a gas; then inflating the balloon and imaging the anatomy surrounding the balloon, then determining whether the cryosurgical probe is in a correct position for cryosurgical ablation based at least in part on the imaging, then, if the determination is that the cryosurgical probe is in a correct position then proceeding with the cryosurgical ablation, and alternatively, if the determination is that the cryosurgical probe is not in the correct position, then repositioning the cryosurgical probe until the cryosurgical probe is in a correct position, as determined at least in part by the imaging, whereby determining correct position may comprise determining the position of a lateral tissue freezing zone of the cryosurgical probe in relation to the adjacent anatomy.

An additional object of this invention is a method for cryosurgical ablation of the function of a nerve comprising inserting a cryosurgical probe between the target nerve and the artery and vein associated with the nerve; with the cryosurgical probe having an elongated structure with a distal end, a proximal end, and at least one central lumen; with said distal end comprising an outer inflatable balloon structure configured as an optical imaging window, and as a tissue dilator enclosing at least one optical imaging device, at least one inner cryogenic evaporator balloon, and at least one inner thermal insulation balloon; with said proximal end comprising a means for introducing a liquid refrigerant into the cryogenic evaporator balloon through a central lumen, a means of removing evaporated refrigerant from the cryogenic evaporator balloon through a central lumen at a predetermined pressure, a means for inflating the thermal insulation balloon with the pressurized evaporated refrigerant gas, a means for connecting the optical imaging device(s) to an imaging display, and a means for inflating the outer balloon with a liquid or a gas; then inflating the outer balloon to create distance between the nerve and the vein and artery; then using the imaging device, position the inner cryo balloon proximate to the nerve, and the inner insulation balloon proximate to the vein and artery; then introducing liquid refrigerant into the cryo balloon causing inflation of the inner cryo balloon and the inner insulation balloon; then maintaining the flow of refrigerant for a period of time sufficient for affecting the nerve function in the desired manner, whereby, the vein and artery remain unaffected by cold due to the separation between the target nerve end the vein and artery, and the thermal insulating effect of the inner thermal insulation balloon.

DETAILED DESCRIPTION OF THE INVENTION

Figure 1:
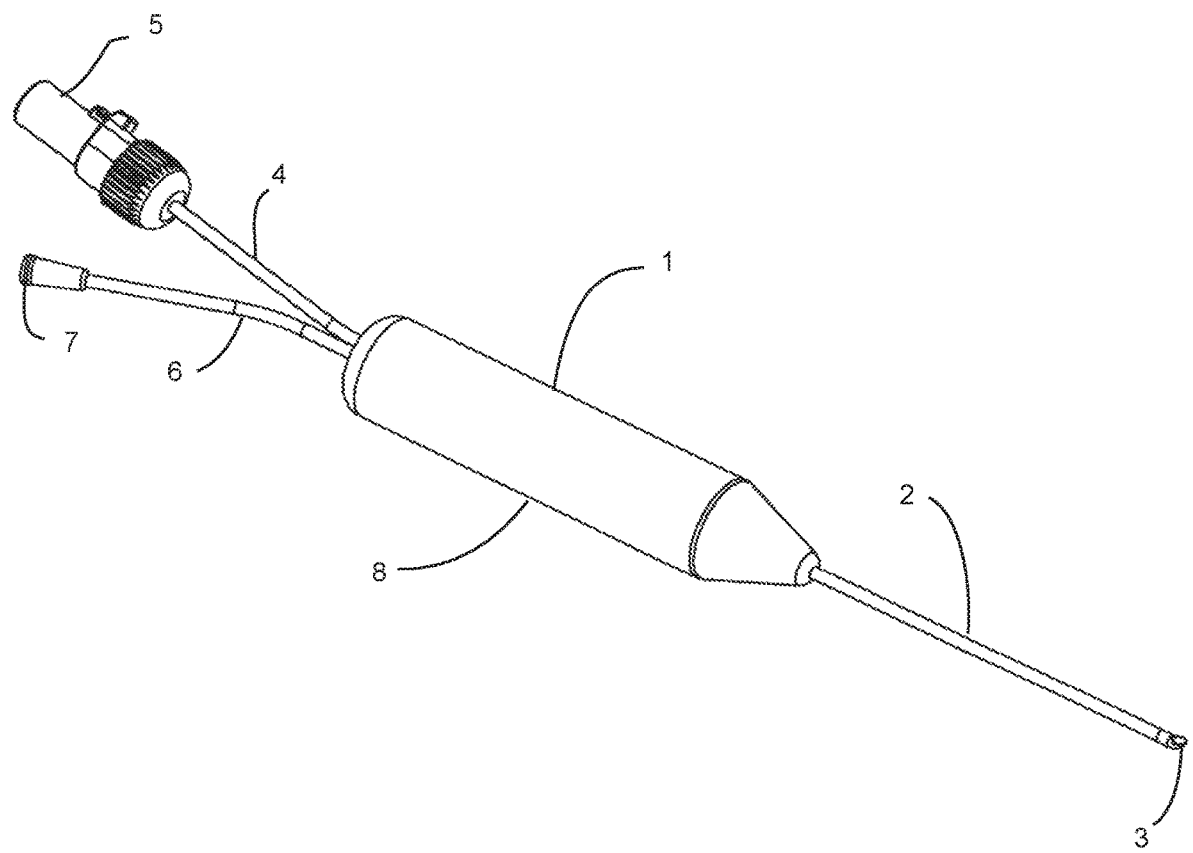
FIG. 1 shows a perspective view of a surgical imaging probe configured for accessing a distal surgical site within a patient using image guidance.

FIG. 1 is an illustration of the central embodiment of surgical imaging probe 1 configured for accessing a distal surgical site within a patient by advancement between anatomical structures by atraumatic blunt dissection using image guidance for the purpose of performing a cryosurgical step. Surgical imaging probe 1 comprises probe shaft 2, non-coring optically transparent needle tip 3, probe handle 8, electrical lead 4, electrical connector 5 fluid tube 6 and fluid connector 7. Probe shaft 2 is between approximately 5 and 20 centimeters long, and between approximately 2.5 and 3.5 millimeters in diameter. Probe shaft 2 has a central lumen between approximately 2.3 and 3.3 millimeters in diameter. Probe shaft 2 may be fabricated from a stainless steel hypodermic tube, or may be fabricated from another metal used in surgical instruments such as titanium. Probe shaft 2 is substantially rigid and is capable of transmitting lateral, longitudinal, and torsional forces along its length. Distal needle tip 3 is configured for blunt atraumatic dissection between the fascias of discrete anatomical structures. Distal needle tip 3 is optically transparent and houses an optical imaging device that is connectable to an imaging display. The optical images are used by the surgeon identify a facial plane through which the surgical probe may safely be advanced towards a target distal region within the body. Distal needle tip 3 also comprises a lateral fenestration which communicates with the interior of distal needle tip 3, and the central lumen of probe shaft 2. Distal needle tip 3, probe shaft 2 are described in greater detail below. Surgical probe handle 8 is configured in an ergonomic manner to provide the surgeon with a comfortable grip of surgical probe 1, and good tactile feedback of the forces resulting from manipulation of surgical probe 1 during the surgery. Surgical probe handle 8 also comprises a means for fluid communication between fluid tube 6 and the central lumen in probe shaft 2. Fluid connector 7 is a female luer fitting as depicted and is configured for connection to a syringe or another fluid source. Additionally, a cryosurgical surgical probe may be inserted through surgical probe 1 for distal use using fluid connector 7, fluid tube 6, the central lumen of probe shaft 5 and exiting through the lateral fenestration of needle tip 3. Electrical lead 4, and electrical connector 5 are configured to connect the optical imaging device mounted within needle tip 3 to an optical imaging display. Electrical lead 4, and electrical connector 5 may provide a means for connecting additional sensors mounted within surgical probe 1 that may include sensors configured to detect temperature, cardiac signals, bodily fluid chemistry, dissecting force, fluid pressure, ionizing radiation, non-visible light, or a magnetic field. Electrical lead 4 and electrical connector may be configured for connecting a therapeutic energy emitting device mounted within surgical probe 1 to a source of therapeutic energy.

Figure 2:
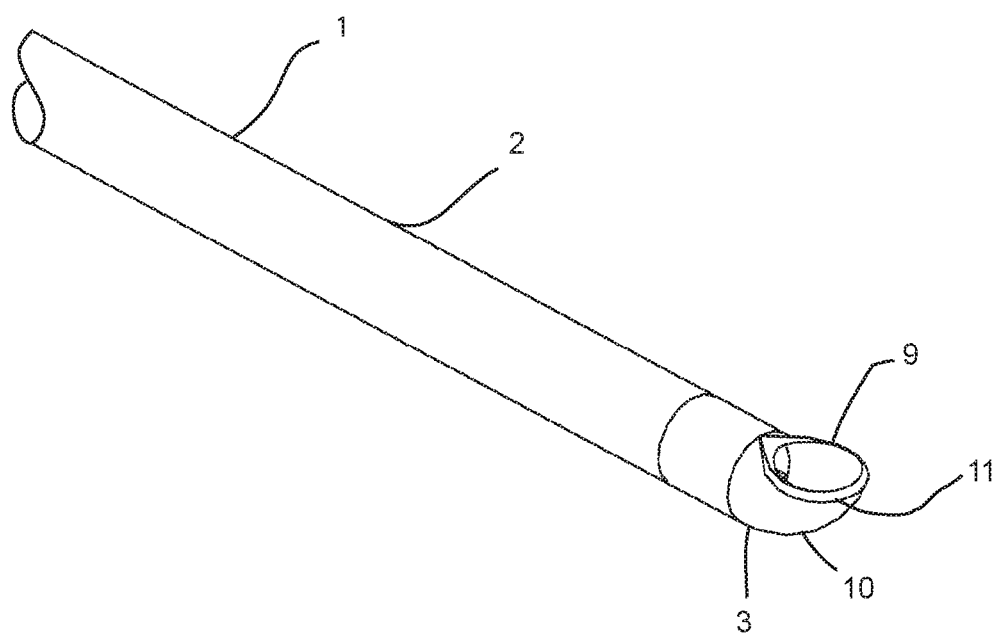
FIG. 2 shows a perspective view of the distal end of the surgical probe having an optically transparent needle tip mounted on the probe shaft.

FIG. 2 is an illustration of the distal end of surgical probe 1 showing the distal end of probe shaft 2, with optically transparent needle tip 3 mounted on probe shaft 2. Needle tip 3 comprises a non-coring needle tip design where the distal face of the needle tip is smooth with a large radius 10 as shown, and comprises a lateral fenestration 9 that communicates between the distal exterior of surgical probe 1 and the interior of needle tip 3 and the central lumen of probe shaft 2. Radiused edge 11 is configured to smooth the edge formed between large radiused surface 10 and fenestration 9 to prevent puncture or incision of tissue as surgical 1 is advanced in the distal direction between anatomical structures.

Figure 3:
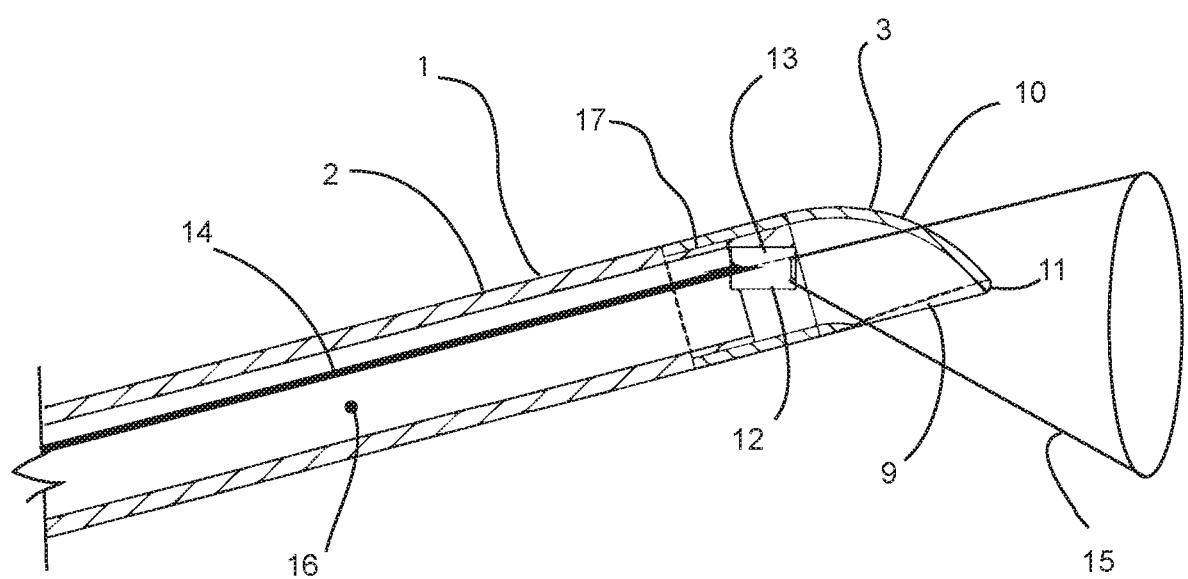
FIG. 3 shows a cross sectional illustration of the distal end of the surgical probe depicting the probe shaft, optically transparent needle tip, and imaging element.

FIG. 3 is a cross sectional illustration of the distal end of surgical probe 1 depicting probe shaft 2, optically transparent needle tip 3, CMOS camera with integral illumination 12, camera mount 13, central lumen 16, electrical cable 14, and camera field of view 15. Probe shaft 2 comprises central lumen 16, and a stepped segment 17 configured for mounting needle tip 3. Needle tip 3 is fabricated from an optically transparent, mechanically rigid material, which may a glass material, or may be a plastic material such as polycarbonate. Those skilled in the art of glass forming, or plastic molding of optical components are familiar the fabrication techniques that may be used for fabricating needle tip 3 as disclosed here within, therefore no further description is warranted. Needle tip 3 is a hollow tubular structure with a central axis substantially aligned with the central axis of probe shaft 2 at its proximal end, and with the central axis substantially perpendicular to the central axis of probe shaft 2 as shown. The distal face is blunt as defined by large radius 10. Fenestration 9 communicates between the interior of needle tip 3 and central lumen 16, and the exterior of surgical probe 1. Fenestration 9 may be configured as shown, or may alternatively be more than one single fenestration. Fenestration 9 may have a diameter that is similar to the diameter of central lumen 16 and suitable for passing a surgical instrument through, or may be substantially smaller than central lumen 16. Camera 12 may be a miniature CMOS camera with integral illumination and similar to cameras offered by Awaiba Corp. which are described in detail at www.awaiba.com, and therefore no further description is warranted here. Camera 12 is mounted to the inner surface of needle tip 3 by camera mount 13, which is configured to point camera 12 so field of view 15 is in the distal direction, and substantially encompasses fenestration 9 as shown. An alternate optical imaging device, not show may be employed for distal imaging, which may be a fiberscope, of a rigid endoscope mounted within central lumen 16. Camera mount 13 may be integrally molded into needle tip 3 as shown, or may be separate component that is bonded to the interior of needle tip 3. Electrical cable 14 connects camera 12 to electrical connector 5 at the proximal end of surgical probe 1, and resides within central lumen 16 as shown.

Figure 4:
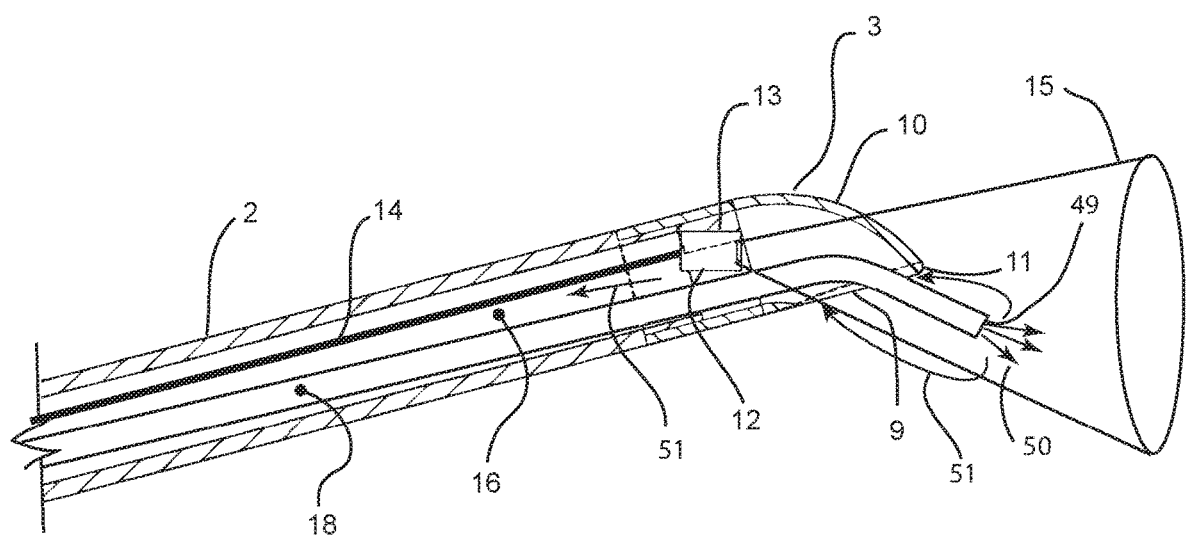
FIG. 4 shows a cross sectional illustration of the distal end of the surgical probe which is configured for direct application of a liquid refrigerant on target tissue within the field of view of the imaging element.

FIG. 4 is a cross sectional illustration of the distal end of surgical probe 1 depicting cryosurgical probe 18, which is configured for direct application of liquid refrigerant on target tissue to effect tissue freezing. As shown cryosurgical probe 18 is extending from central lumen 16 and needle tip 3 in position for spraying liquid refrigerant 50 through distal cryo-nozzle 49 on target distal tissue within the field of view 15 of camera 12. Also as depicted, evaporated refrigerant 51 is vented back to ambient atmosphere through central lumen 16. Camera 12 may be used to monitor and guide tissue freezing. Cryosurgical probe 18 may comprise a steerable distal segment that may be utilized to direct the spray of liquid refrigerant. Those skilled in the art of steerable catheters are familiar with designs and manufacturing process for incorporating steerable function into cryosurgical probe 18, therefore no further description is warranted.

Figure 5A:
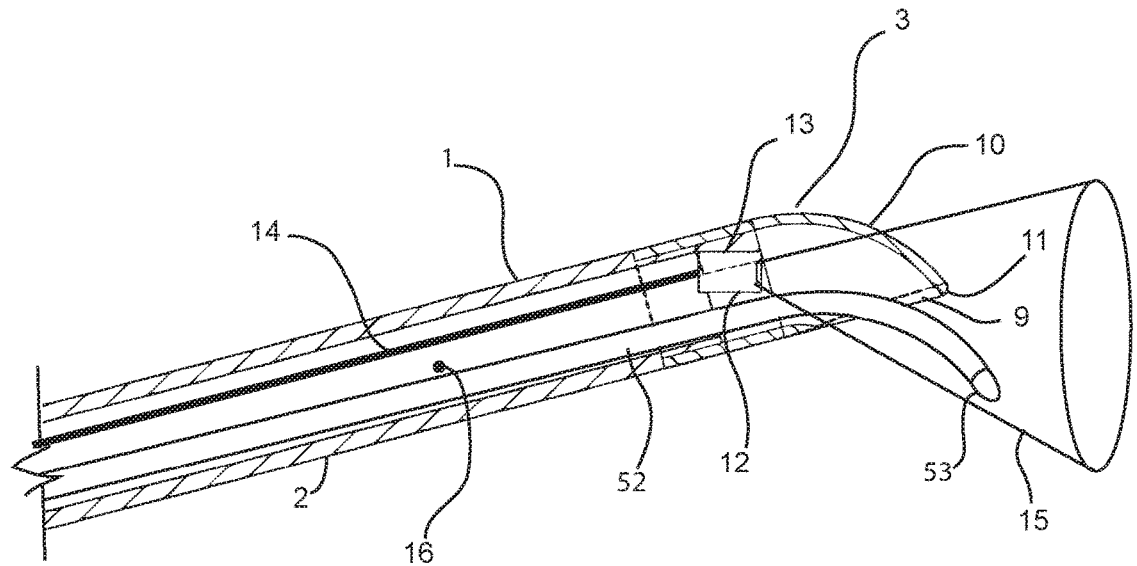
FIGS. 5A and 5B show cross sectional side views of the distal end of the surgical probe illustrating a cryosurgical balloon probe having a balloon member which is inflatable upon introduction of a liquid refrigerant.
Figure 5B:
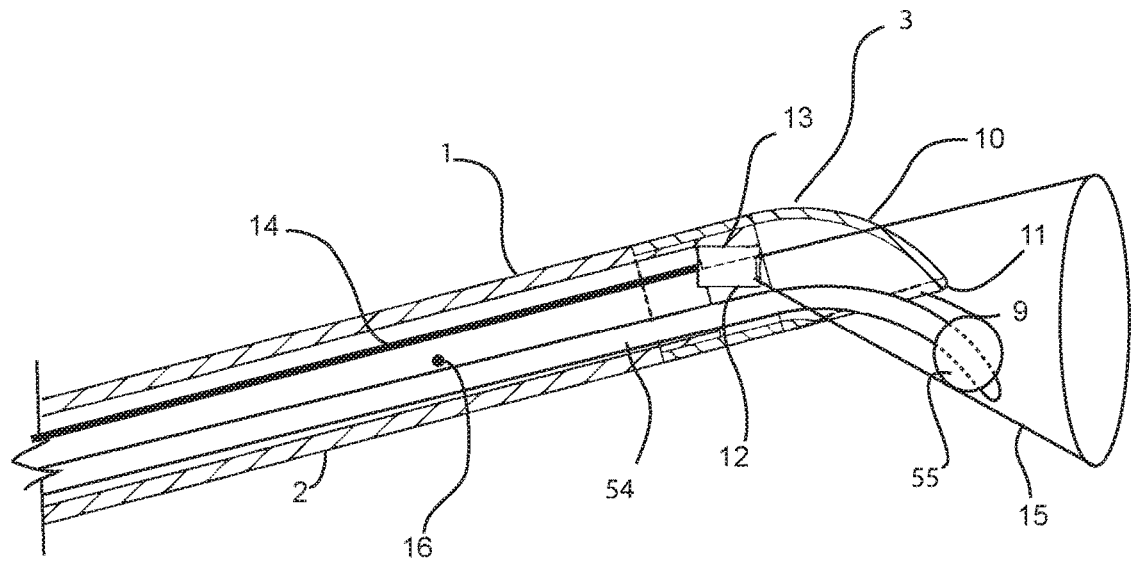

FIG. 5A is a cross sectional illustration of the distal end of surgical probe 1 configured for distal tissue ablation utilizing cryosurgical probe 52 comprising a closed distal evaporator chamber 53, which freezes target tissue by contact with the surface of evaporator 53, and by thermal conduction of heat from the target tissue into evaporator chamber 53. Cryosurgical probes with closed distal evaporation chambers are thoroughly and widely described in the prior art, therefore no further description of cryosurgical probe 52 is warranted. FIG. 5B is a cross sectional illustration of the distal end of surgical probe 1 configured for distal tissue ablation utilizing cryosurgical balloon probe 54 comprising a closed distal evaporator balloon chamber 55, which inflates upon introduction of liquid refrigerant into the interior of balloon 55 and freezes target tissue by contact with the surface of balloon 55, and by thermal conduction of heat from the target tissue into evaporator balloon chamber 55. Cryosurgical probes with closed distal evaporation balloon chambers are thoroughly and widely described in the prior art, therefore no further description of cryosurgical probe 54 is warranted.

Figure 6A:
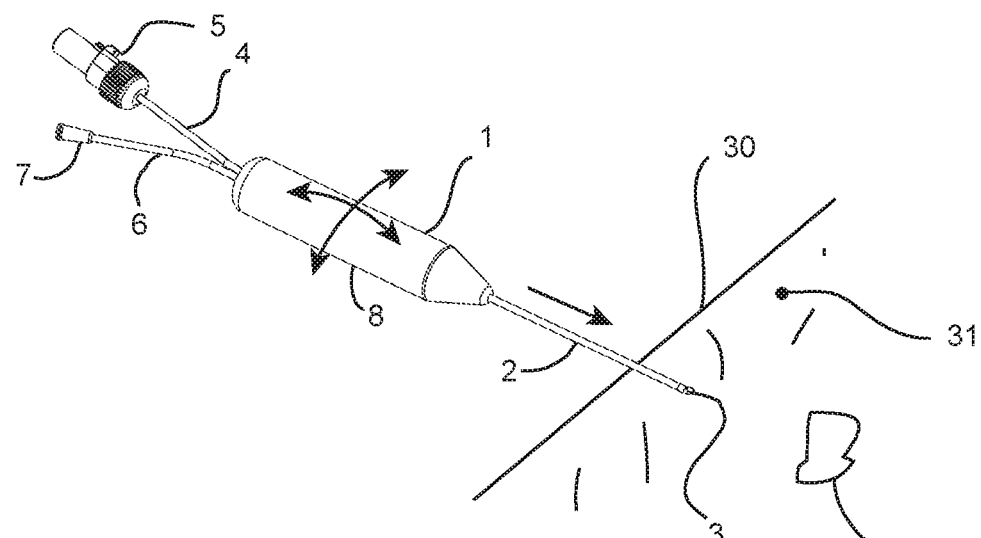
FIG. 6A shows a schematic illustration of a surgical probe inserted into the body of a patient and advanced through tissue towards the target distal region while under visual guidance.
Figure 6B:
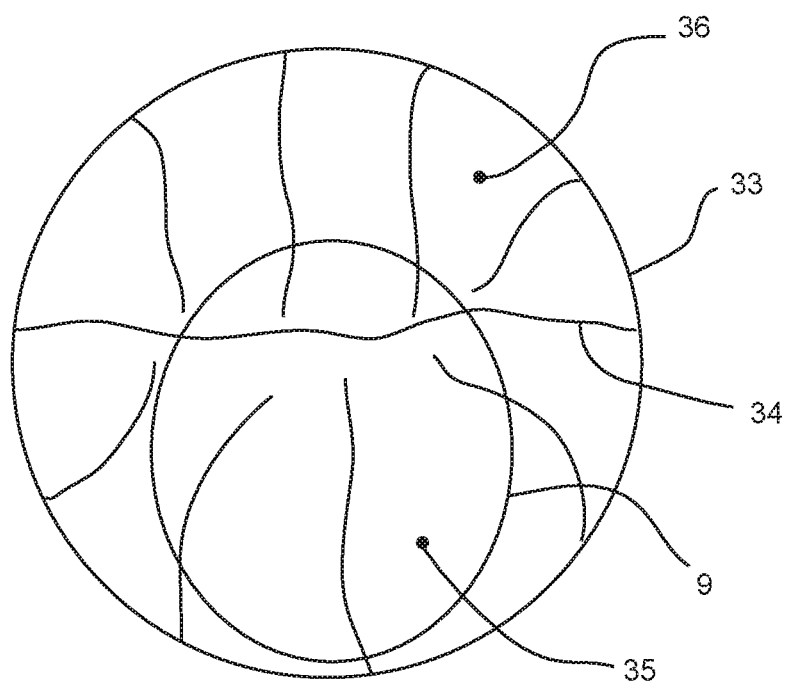
FIG. 6B shows an illustration of an image received from the imaging element positioned within the probe.
Figure 6C:
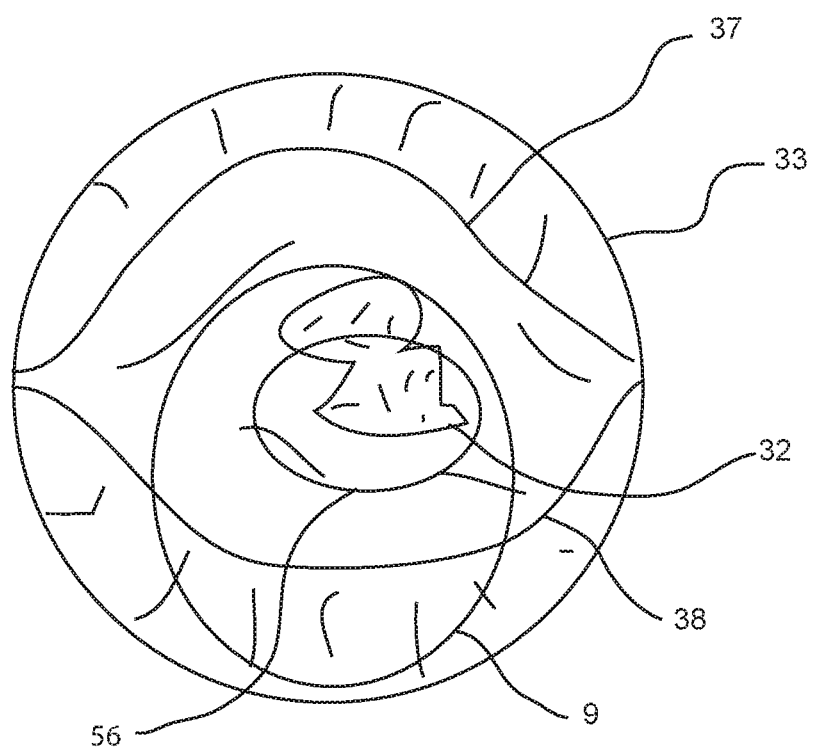
FIG. 6C shows an illustration of an image from imaging element showing the target distal region residing between facial surfaces which have been separated by the manipulation of the surgical probe.

FIG. 6A is a schematic illustration of surgical probe 1 being inserted into the body of a patient 30 and being advanced in a distal direction through tissue 31 towards target distal region 32 under visual guidance. Surgical probe 1 may be manipulated in torsional and lateral directions as represented by the crossed arrows in order to find a facial boundary between two or more discrete anatomical structures through which surgical probe 1 may be safely advanced in the distal direction towards the target distal region 32. FIG. 6B is an illustration showing an image from camera 12. Visible in the image is distal tissue comprising discrete anatomical structures 36, and 35, which is separated by facial boundary 34. Fenestration 9 is shown in full view. FIG. 6C is an illustration showing an image from camera 12 showing the target distal region 32 residing between facial surfaces 37 and 38, which have been separated by the manipulation of surgical probe 1 facilitating one or more surgical therapeutic or diagnostic step(s), including a possible cryosurgical step, as depicted by frozen tissue 56.

Figure 7A:
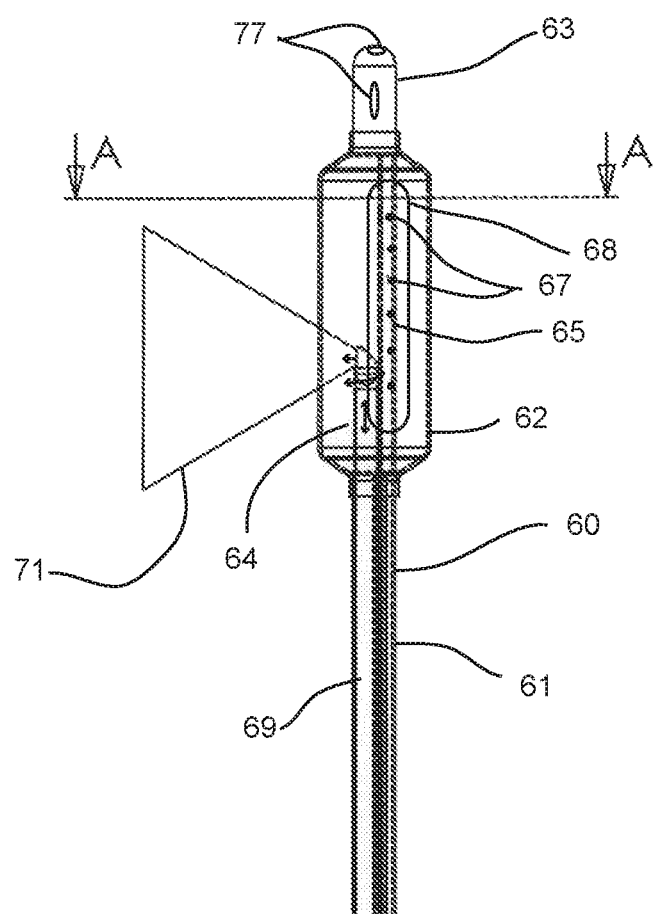
FIG. 7A shows a side view of a variation of the distal end of an Image Guided Directed Cryosurgical Balloon (IGCB) probe.
Figure 7B:
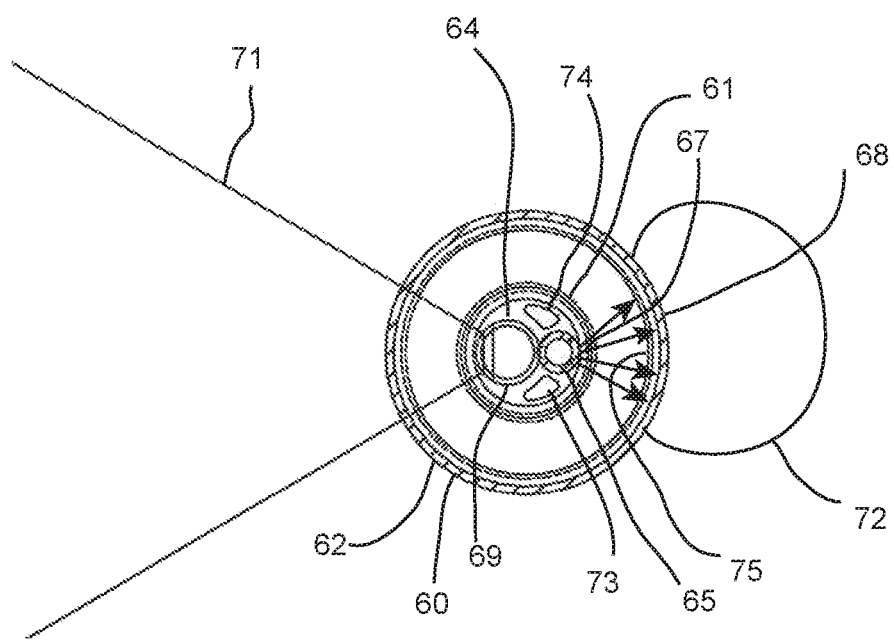
FIG. 7B shows a cross sectional end view of the IGCB probe.
Figure 7C:
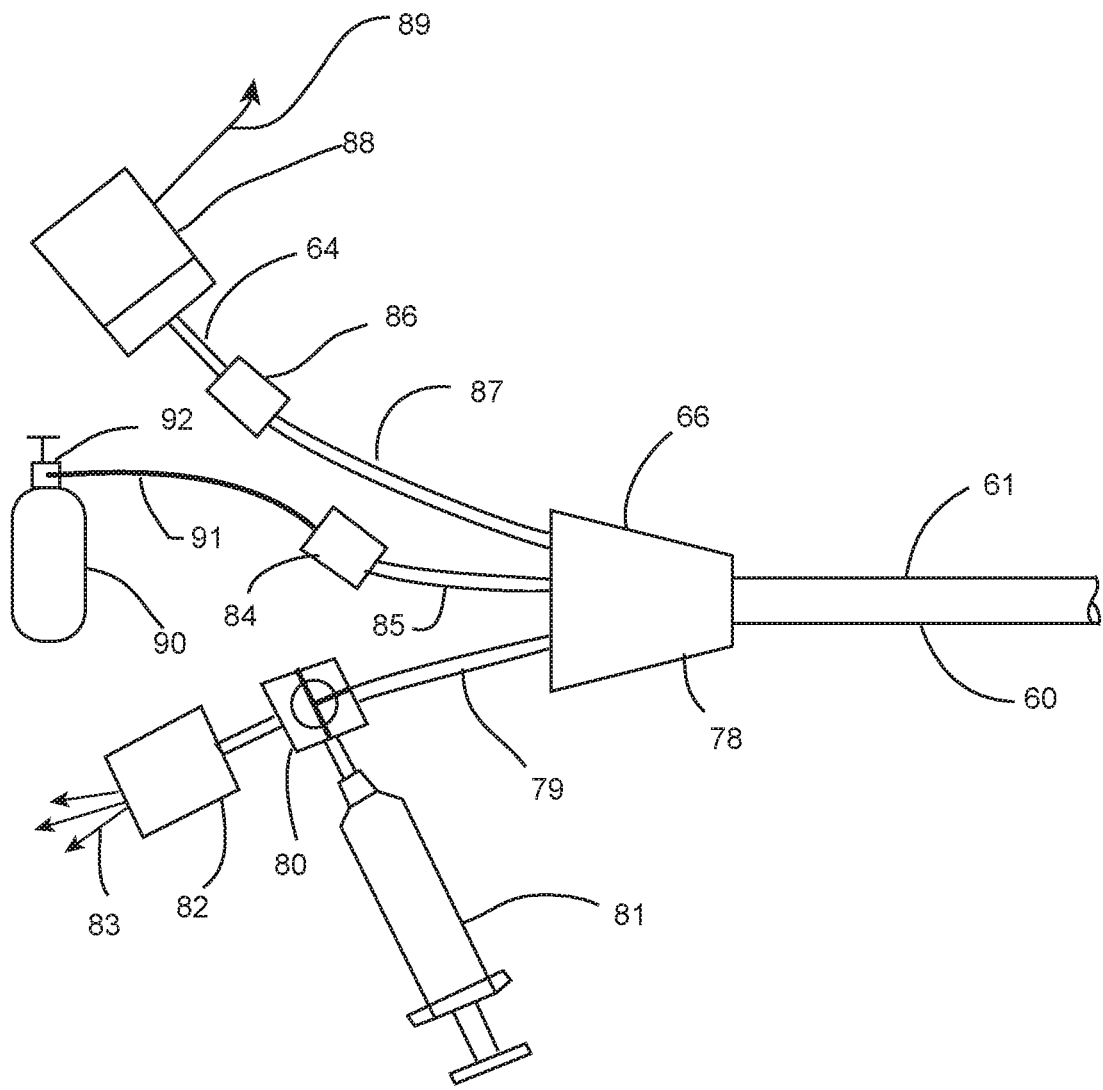
FIG. 7C shows a schematic illustration of a variation of the proximal terminal of the IGCB probe.

FIGS. 7A, 7B and 7C are schematic illustrations of Image Guided Directed Cryosurgical Balloon (IGCB) probe 60. IGCB Probe 60 comprises probe shaft 61, balloon 62, distal tip 63, optical imaging probe 64, cryogen tube 65, and proximal terminal 66.

FIG. 7A depicts the distal end of IGCB probe 60 showing balloon 62 bonded to probe shaft 61 at its proximal end, and bonded to distal tip 63 at its distal end. Also shown is cryogen tube 65 mounted between probe shaft 61 and distal tip 63. Cryogen tube 63 comprises a linear array of lateral cryogen nozzles 67. Lateral cryogen nozzle array 67 are small fenestrations through on wall of cryogen tube 65, and are between approximately 50 and 150 microns in diameter, and number between one and approximately 20 or more. Lateral cryogen nozzles 67 may formed by a laser machining operation. Cryogen tube 65 is connectable to a source of cryogenic liquid at proximal terminal 66, and is configured to spray a lateral region of balloon 62 with liquid cryogen to form lateral tissue freezing zone 68. Cryo tube 65 and balloon 62 are configured so that substantially all of the liquid cryogen sprayed at the inner wall of balloon 62 is evaporated on contact, and balloon 62 is substantially filled with cryogen in a gaseous state, which is thermally insulative, thereby limiting tissue freezing to tissue adjacent to tissue freezing zone 68. Cryo tube 65 is also configured to mechanically link probe shaft 61 to distal tip 63 and to translate axial and lateral forces between probe shaft 61 and distal tip 63 to a degree sufficient to maneuver IGCB probe 60 into position within a mammalian body for the purpose of performing at least one cryosurgical step. The inner lumen of cryogen tube 65 is terminated and sealed at distal tip 63, thereby, all cryogen leaves cryogen tube 65 through lateral cryogen nozzle array 67. Cryogen tube 65 may be fabricated from stainless steel or Nitinol® hypodermic tube. Optical imaging probe 64 may be removably inserted into the interior of balloon 62 though central lumen 69, and imaging port 70 of proximal terminal 66 (See FIG. 7C). Optical imaging probe 64 is configured for lateral imaging as depicted by imaging field of view 71. Optical imaging probe 64 and IGCB probe 60 are configured with an imaging range of motion that is substantially 360 degrees of lateral imaging, and with an axial range that approximates the length of the balloon 62. Imaging probe 64 is described in greater detail below. Balloon 62 is configured for tissue dilation, and as an optical window for optical imaging probe 64. Balloon 62 may be fabricated from a substantially in-elastic material with good optical clarity such PET. Balloon 62 is configured to have a burst strength of between approximately 4 and 12 atmospheres of pressure, at a cryogenic temperature between zero, and minus 100 degrees centigrade. Balloon 62 is bonded using an adhesive to the distal end of probe shaft 61, and the proximal end of distal tip 63 as shown. Balloon 62 may be inflated (as shown) with a liquid or a gas though at least one central lumen in probe shaft 61, and a fluid port on proximal terminal 66, which is described in detail below. Balloon 62 may also be inflated during cryogen spraying using the expansion of the evaporating cryogen and a pressure regulating valve mounted within distal terminal 66 disposed between the interior of balloon 62 and the ambient atmosphere, which is described in more detail below. Those skilled in the art of surgical balloon probe design and manufacture are familiar with means for designing and manufacturing IGCB probe as disclosed here within, therefore, no further explanation is warranted. Probe shaft 61 may be substantially rigid, and fabricated as a metal extrusion, or may be substantially flexible and fabricated from a plastic material such as urethane, PeBax®, nylon, or polyethylene. Distal tip 63 may be bullet shaped as shown, and may have a guidewire channel 77 as shown for assisting in positioning IGCB probe 60 into position for performing a cryosurgical step. Distal tip 63 may be a molded or extruded plastic material, or may be machined from metal.

FIG. 7B is a sectional illustration taken at section A-A in FIG. 7A. Depicted in FIG. 7B is cryogen 75 being sprayed against a lateral section of balloon 62 (lateral tissue freezing zone 68) through lateral cryogen nozzle array 67 in cryogen tube 65. Also shown is ice ball 72 formed in tissue adjacent to lateral tissue freezing zone 68. Optical imaging probe 64 is shown imaging tissue diametrically opposed to lateral tissue freezing zone 68. Also depicted are balloon lumens 73 and 74 which are in fluidic communication with proximal terminal 66. Balloon lumens 73 and 74 may be used to together or separately for inflating the balloon with a liquid or gas prior to or after tissue freezing, and are used to vent evaporated cryogen from balloon 62.

FIG. 7C is a schematic illustration of proximal terminal 66 of IGCB probe 60. Hub 78 fluidically connects balloon lumens 73 and 74 to balloon lumen hub tube 79, cryogen tube 65 to cryogen hub tube 85, and provides an insertion path for optical probe 64 into optical probe lumen 69 though optical probe port 86 and optical probe hub tube 87. Hub 78 in insert molded using mandrels to create discrete channels between the hub tubes and lumens described above. Those skilled in the art of surgical probe hub design and manufacture are familiar methods for designing and manufacturing the an IGCB probe hub as disclosed here within, therefore no further description is warranted. Imaging probe 64 is inserted into imaging probe lumen 69 through imaging probe port 86 and imaging probe hub tube 87. Imaging probe port 86 may comprise a Toughy Borst connector, or another type of surgical pressure port. Imaging module 88 comprises a camera and a light source. The camera images the proximal end of the coherent optical fiber bundle of imaging probe 64, and the light source provides illumination to the distal surgical field, with the light being transmitted distally by a second optical fiber or fiber bundle. Optical imaging probe 64 will be described in further detail below. Imaging module 88 is connected to an imaging display, not shown. Cryogen tube 65 is connected to a source of liquid cryogen 90 by means of cryogen port 84, cryogen source hose 91, and cryogen connector 92. Liquid cryogen source 90 is depicted schematically as a cryogen tank. The liquid cryogen source may comprise a control console that controls the flow of cryogen based on user settings, and feedback from sensors, not shown. The liquid cryogen may be liquid carbon dioxide or liquid nitrogen, or a liquid chlorofluorocarbon compound. Alternatively, instead of using evaporative cooling, a Joules-Thompson effect (adiabatic gas expansion) cooling architecture could employed and still be within the scope of this invention. Nitrous oxide or argon gas would be the preferred cryogenic gasses for use if a Joule-Thompson cooling architecture is employed. Those skilled in the art cryosurgical probe design and manufacture are familiar the design attributes and trade-offs between liquid cryogen evaporative cooling and Joule-Thompson effect cooling architectures, and are familiar with the means for employing either cooling architecture within the scope of this invention, therefore no further discussion is warranted. Balloon lumens 73 and 74 are in fluidic communication with balloon lumen hub tube 79. Stop cock 80 provides the user a means to either inflate balloon 62 prior to or after a cryosurgical step using syringe 81. Syringe 81 may also be used to deflate balloon 62.

During a cryosurgical step, the stop cock is configured to fluidically connect pressure relief valve 82 to balloon lumen hub tube 79, and fluidically disconnect syringe 81 from balloon lumen hub tube 79. Pressure relief valve 82 vents evaporated cryogen 83 to the ambient atmosphere while maintaining a set pressure with balloon 62 during liquid cryogen delivery. The pressure created by pressure relief valve 82 is used to maintain inflation and tissue dilation force for balloon 62 in order to maintain a spatial separation between tissue targeted for freezing, and tissue intended to be protected from freezing. Pressure relief valve 82 may have a fixed preset pressure relief setting, or pressure relief valve 82 may have a user adjustable pressure setting within a range of pressures that are lower than the burst strength of balloon 62. Pressure relief valve 82 may also comprise an audible indication of the volumetric flow rate of evaporated cryogen 83 exiting pressure relief valve 82. The audible indication may be in the form of a whistle where the pitch or volume of the whistle may increase as the flow rate of evaporated cryogen 83 increases. The audible signal may provide the user with an indication of tissue freezing effectiveness, or an indication of device failure, such as a cryo balloon 62 failure.

Figure 8:
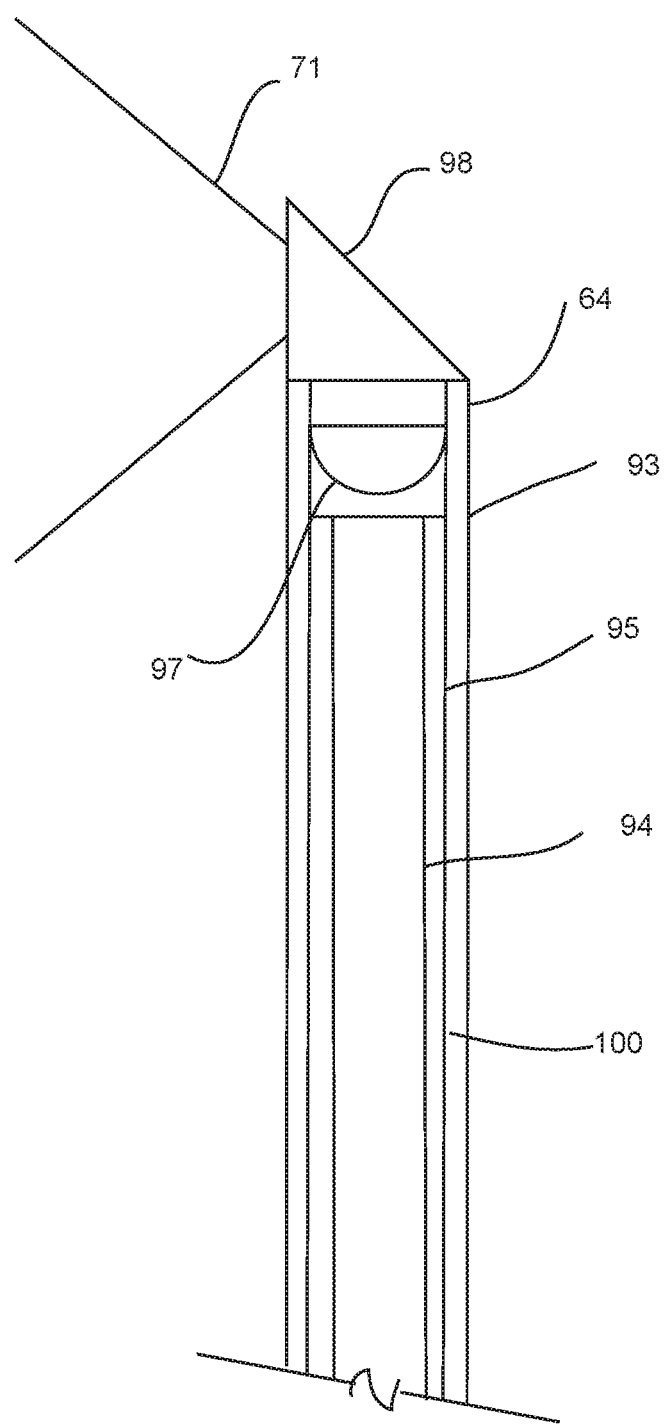
FIG. 8 shows a cross sectional schematic side view of a variation of the distal end of a lateral optical imaging probe.

FIG. 8 is a cross sectional schematic illustration of the distal end of lateral optical imaging probe 64. Lateral optical imaging probe 64 comprises imaging probe sheath 93, fiber bundle 100 comprising central coherent fiber bundle 94 and outer non-coherent fiber bundle 95, and imaging element 96 comprising objective lens 97, lateral reflective surface 98, and imaging window 99. Imaging probe sheath 93 houses optical fiber bundle 100, and is used to mount imaging element 96 at the distal end of lateral optical imaging probe 64. Imaging probe sheath 93 may fabricated from a thin walled polyimide tubing. The outer diameter of optical imaging sheath 92 is between approximately 0.8 mm and 1.5 mm in diameter, with a length suitable to the particular IGCB probe, which may vary based on specific surgical requirements. Imaging element 98 is machined from optical grade glass forming objective lens 97, lateral reflecting surface 98 and optical imaging window 99. Objective lens 97 creates an image of the anatomical surroundings within field of view 71 on the surface of coherent optical bundle 94. A camera within imaging module 88 at the proximal end of lateral optical imaging probe 64 converts the image to video image for surgical guidance. Non-coherent fiber optical bundle 95 transmits light from a light source within proximal imaging module 88 to illuminate field of vision 71. Lateral reflecting surface 98 may be a mirror coated surface, or may function as a prism. Those skilled in the art of fiber scopes, and optical engineering are familiar with means for designing and developing a lateral optical imaging as disclosed here within, and remain within the scope of this invention, therefore, no further description is warranted.

Figure 9A:
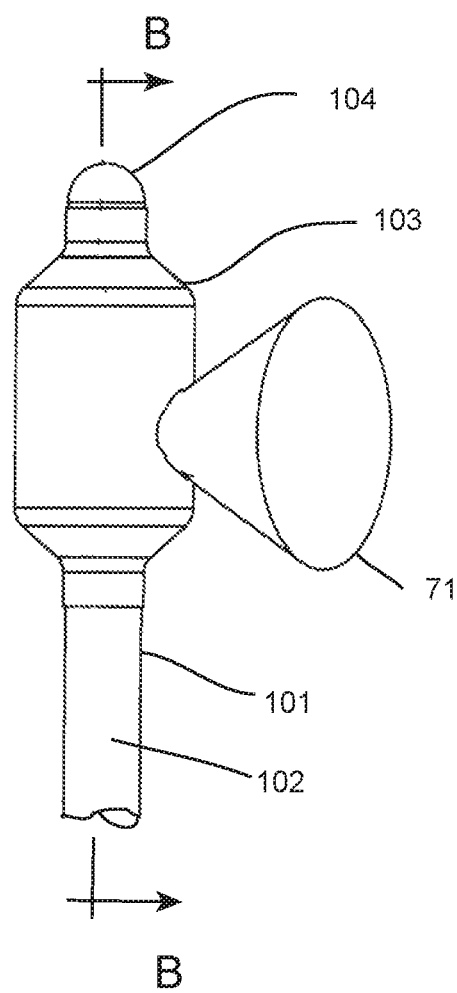
FIG. 9A shows the distal end of the IGCB probe with an inflated outer balloon and a lateral optical imaging probe imaging the surrounding anatomy from within the outer balloon as represented by field of view.
Figure 9B:
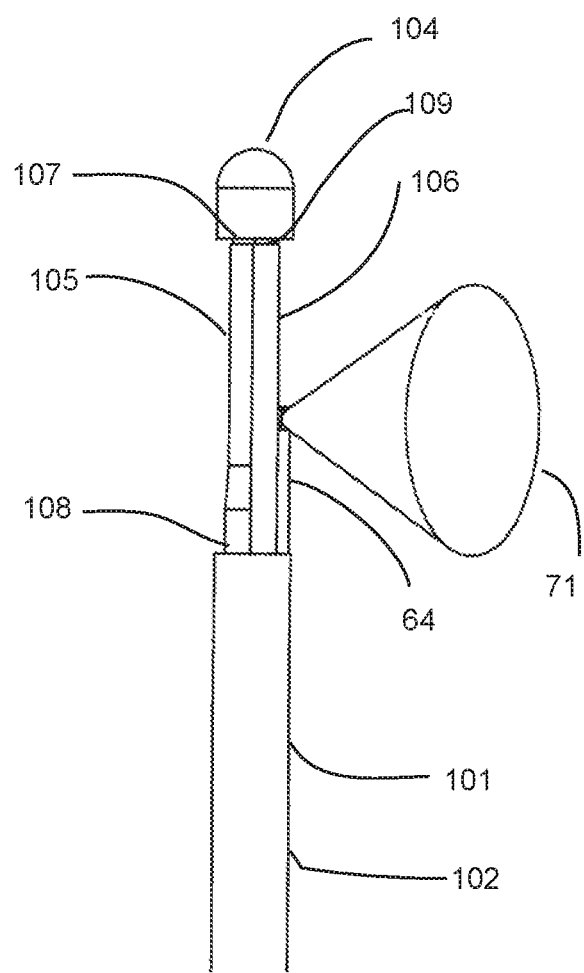
FIG. 9B shows the distal end of IGCB probe 101 with the outer balloon removed for clarity to reveal an inner cryo balloon in a deflated configuration and an inner thermal insulation balloon in a deflated configuration.
Figure 9C:
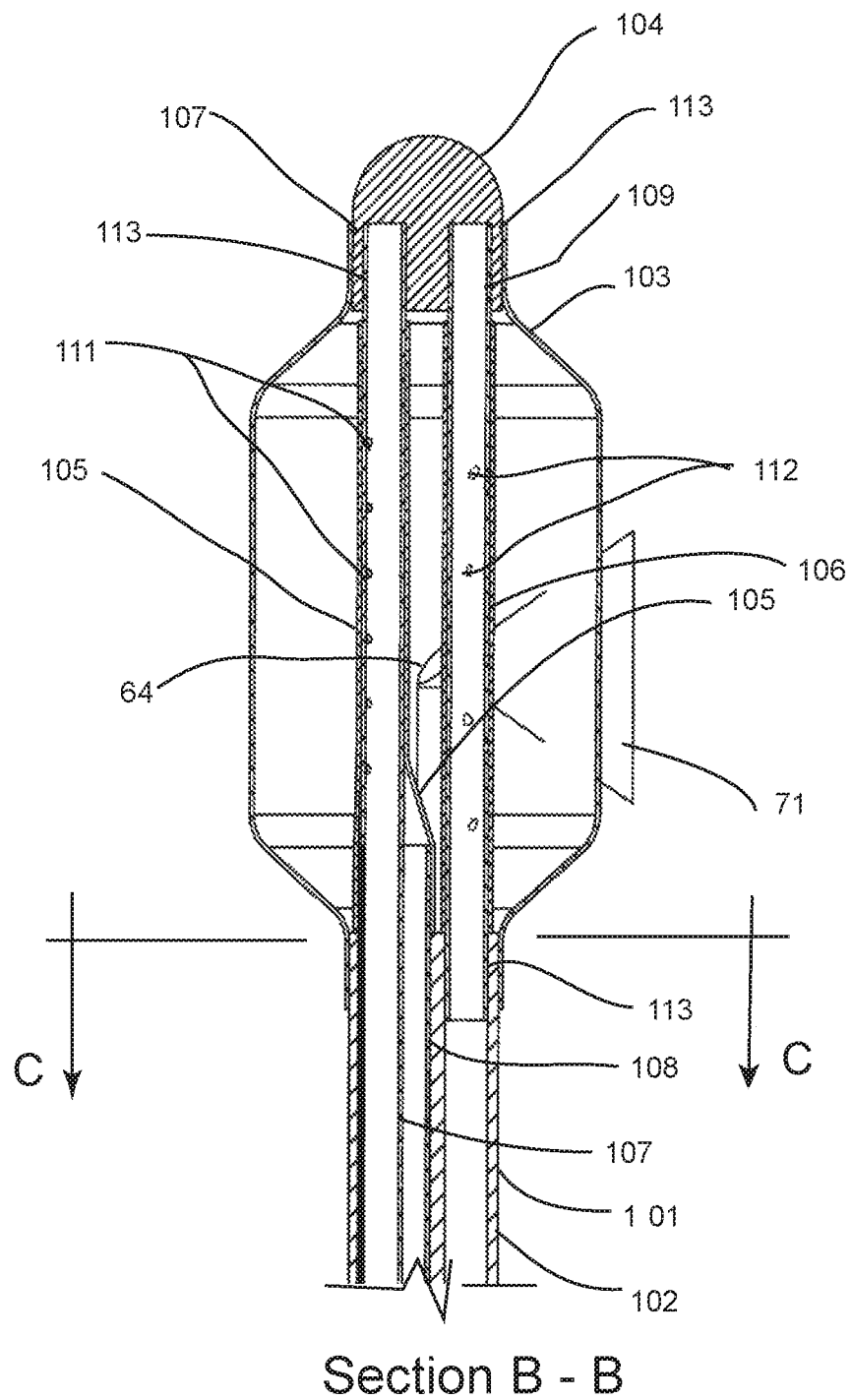
FIG. 9C shows a cross sectional side view of the distal end of the IGCB probe.

FIGS. 9A, 9B, and 9C are schematic illustrations of the distal end of Image Guided Cryo Balloon (IGCB) probe 101, which is an alternative embodiment to IGCB probe 60. IGCB probe 101 comprises probe shaft 102, outer balloon 103, distal tip 104, inner cryo balloon 105, inner thermal insulation balloon 106, cryogen balloon tube 107, insulation balloon tube 109, lateral optical imaging probe 64, with lateral field of view 71, and cryogen vent tube 108, and proximal terminal 109, which will be described in detail below.

FIG. 9A shows the distal end of IGCB probe 101, with outer balloon 103 inflated, and lateral optical imaging probe 64 imaging the surrounding anatomy from within outer balloon 103, as represented by field of view 71. The proximal end of outer balloon 103 is bonded to the distal end of probe shaft 102, and the distal end of outer balloon 103 is bonded to the proximal end of distal tip 104. FIG. 9B shows the distal end of IGCB probe 101 with outer balloon 103 hidden, revealing inner cryo balloon 105 in a deflated configuration, inner thermal insulation balloon 106 in a deflated configuration, with cryo balloon tube 107, and inner insulation balloon tube 109 mounted between distal tip 104 and probe shaft 102. Also depicted is lateral optical imaging probe 64 with field of view 71. FIG. 9C is a cross sectional view of the distal end of IGCB probe 101 taken at section marks B-B in FIG. 9A. Cryogen nozzle array 111 is directs and meters liquid cryogen into inner cryogen balloon 105. Cryo nozzle array 111 is an array of small fenestrations in the wall of cryogen balloon tube 107, and are between 50 and 150 microns in diameter, and number between one and approximately 20, all located within the interior of inner cryo balloon 105. Vent ports 112 are fenestrations in the wall of inner insulation balloon tube 109 and provide fluidic communication between the inner lumen of inner insulation balloon tube 109 and the interior of inner thermal insulation balloon 106. Inner cryo balloon 105, and inner thermal insulation balloon 106 are substantially elastic balloon, and are preferably made from a silicone rubber. Outer balloon 103 is substantially non-elastic, and is optically clear, and is preferably made from PET. The distal end of outer balloon 103 is bonded to the proximal end of distal tip 104 using adhesive 113. The proximal end of outer balloon 103 is bonded to the distal end of probe shaft 102 using an adhesive 113. The distal end of cryo balloon 105 is bonded to the distal end of cryogen balloon tube 107, just proximal to distal tip 104 using adhesive 113. The proximal end of inner cryo balloon 105 is bonded to the distal end cryogen vent tube 108 using adhesive 113 as shown. the distal end of inner thermal insulation balloon is bonded to the distal end of inner insulation balloon tube at its distal end just proximal to distal tip 104 using adhesive 113 as shown. The proximal end of inner insulation balloon 106 is bonded to inner insulation balloon tube 109 just distal to probe shaft 101 using adhesive 113 as shown. Adhesive 113 may be any suitable adhesive. Outer balloon 103 has a burst strength between approximately 4 and 12 atmospheres of pressure. Inner cryo balloon 105, and inner thermal insulation balloon 106 have a burst strength of approximately 2 atmospheres of pressure or less. Cryo vent tube 108 and inner insulation balloon tube 109 are in fluidic communication at proximal terminal 110. When liquid cryogen is introduced into inner cryo balloon 105 through cryogen nozzle array 111, inner cryo balloon 105, and inner thermal insulation balloon 106 are pressurized due to the evaporation of cryogen causing both inner cryo balloon 105, and inner thermal insulation balloon 106 to be inflated and to conform to the inner surface of outer balloon 103. The pressure of inflation is controlled by a pressure relief valve in proximal terminal 110, and is described in further detail below. Outer balloon 103 may be inflated or deflated independently of of the introduction of cryogenic liquid into inner cryo balloon 105. The outer diameter of outer balloon 103 is between approximately 6 mm and 20 mm or more. The length of outer balloon 103 is between 1 cm and 6 cm or more. The dimensions of inner cryo balloon 105 and inner thermal insulation balloon 106 are sized so that both balloons are in conformity with the interior outer balloon 103 when pressurized. Inner cryo balloon 105 is configured to freeze tissue laterally in a radial segment of outer balloon 103 between approximately 90 and 270 degrees. Inner insulation balloon 106 is configured to prevent tissue freezing in a radial segment of outer balloon 103 between approximately 90 and 270 degrees. The radial segments of tissue freezing and tissue insulation may manipulated by the dimensions of inner cryo balloon 105 and inner thermal insulation balloon 106, and manipulation of their material properties, including elasticity. Lateral optical probe 64 may be inserted into and withdrawn from outer balloon 103, prior to a cryosurgical step, and after a cryosurgical step.

Figure 10:
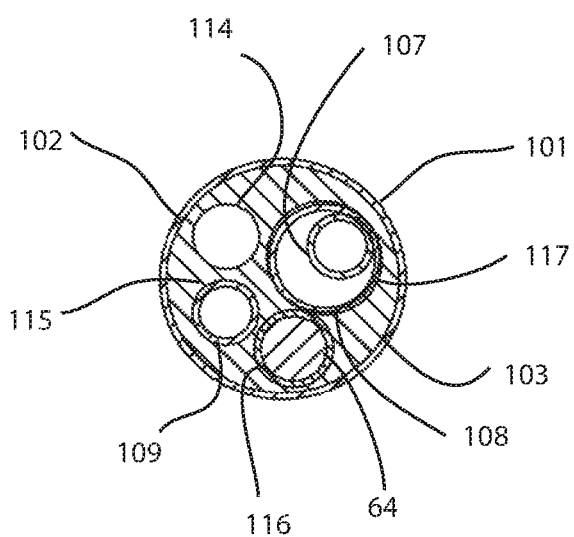
FIG. 10 shows a cross sectional end view of the IGCB probe taken proximal to the inflatable outer balloon.

FIG. 10 is a cross section Illustration of IGCB probe 101 taken at section C-C of FIG. 9C. Probe shaft 102 may me substantially rigid and extruded of a surgical metal, or may be substantially flexible and extruded from a plastic material such as urethane, PeBax®, nylon or polyethylene. The diameter of probe shaft 102 is between approximately 2.5 and 3.5 mm. The length of probe shaft 102 is application specific and may range between 10 cm and 100 cm or more. Probe shaft 102 comprises outer balloon lumen 114, inner thermal insulation balloon lumen 115, imaging probe lumen 116, and inner cryo balloon lumen 117. Inner insulation balloon tube 109 resides within inner thermal insulation balloon lumen 115 for at least a portion of the length of probe shaft 102. Inner insulation balloon tube 109 may be bonded within inner thermal insulation balloon lumen 115 with an adhesive. Lateral optical imaging probe 64 is configured to reside within optical imaging lumen 116, and may be inserted and withdrawn form optical imaging lumen 116 from a port in proximal terminal 110, which will be described in further detail below. Cryo tube 107 resides within cryo vent tube 108 in a coaxial relationship as shown. Cryo vent tube 108 resides within inner cryo balloon lumen 117 as shown. Inner cryo balloon tube 105, and inner thermal insulation balloon tube 109 may be fabricated from a stainless steel of Nitinol® hypodermic tube. Cryo vent tube 108 may be fabricated from a plastic extrusion, or a metal hypodermic tube. The inner cross sectional area of inner cryo balloon tube 107 is approximately less than one half of the inner cross sectional area of cryo vent tube 108.

Figure 11:
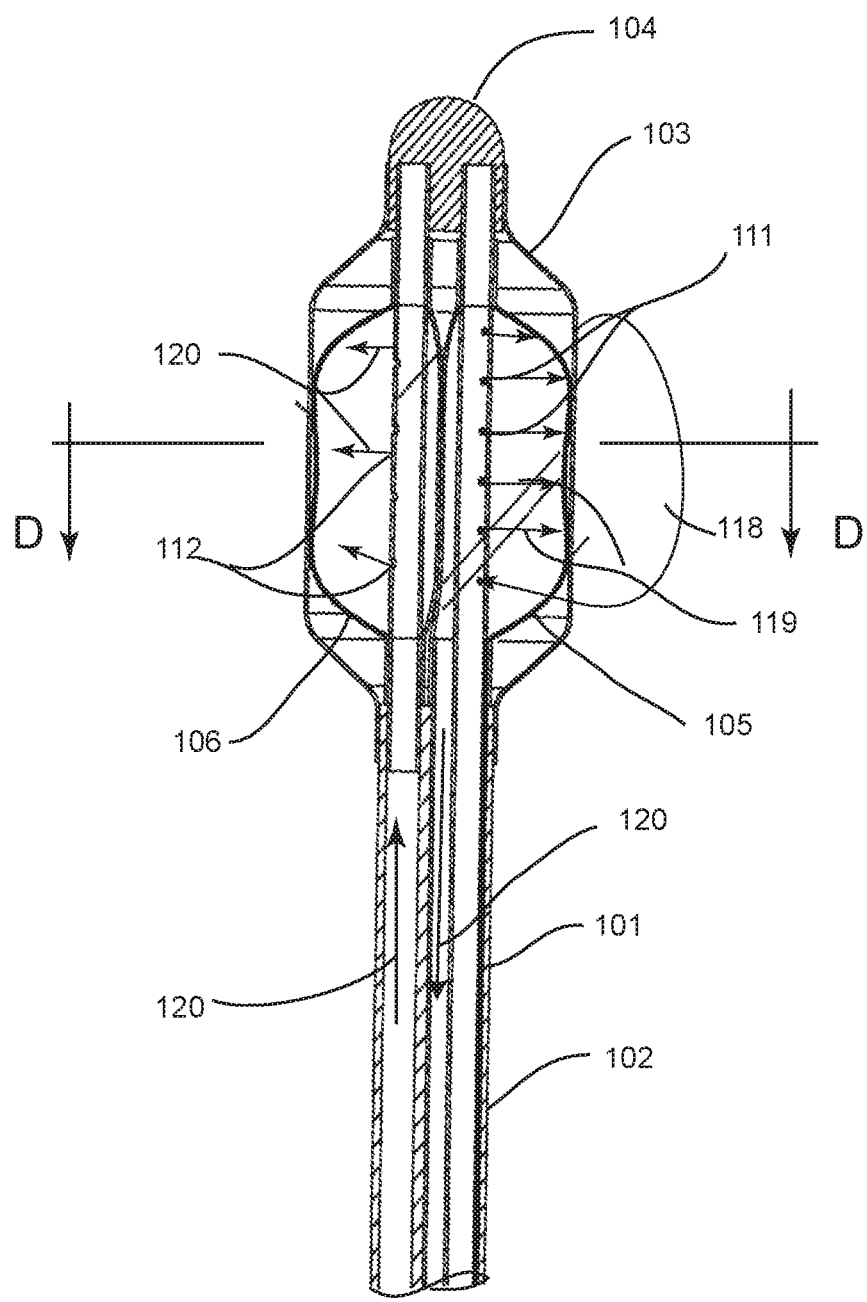
FIG. 11 shows a cross section side view of the distal end of the IGCB probe during a cryosurgical procedure.

FIG. 11 is a cross section schematic illustration of the distal end of IGCB probe 101 during a cryosurgical step. Lateral optical imaging probe 64 has been withdrawn from the interior of outer balloon 103. Liquid cryogen 119 is shown being sprayed at the lateral wall of inner cryo balloon 105. As a result of the evaporation of liquid cryogen 119 inner cryo balloon 105, and inner insulation balloon 106 are inflated at a pressure controlled by a pressure relief valve in the proximal terminal 110 by evaporated cryogen gas 120, into substantial conformance to the inner surface of outer balloon 103. Ice ball 118 is formed within the tissue adjacent to inner cryo balloon 105. Tissue adjacent to inner thermal insulation balloon 106 is spared from freezing, and therefore freezing injury.

Figure 12:
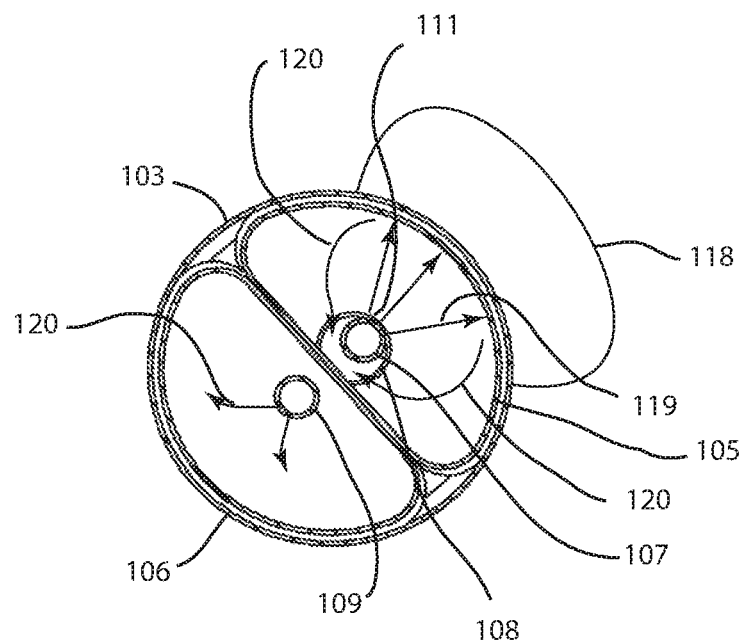
FIG. 12 shows a transverse cross sectional end view of the IGCB probe illustrating cryogenic fluid being sprayed at an inner wall of the inner balloon.

FIG. 12 is a transverse cross sectional schematic illustration of IGCB probe 101 taken at section D-D of FIG. 11. Depicted is liquid cryogen 119 being sprayed at the inner wall of inner cryo balloon 105 by cryogenic nozzle array in inner cryo balloon tube 107. As a result, liquid cryogen 119 evaporates at the surface of inner cryo balloon 107 forming cryogenic gas 120, that is maintained at a pressure sufficient to inflate inner cryo balloon 105 and inner thermal insulation balloon 106 into conformance with the interior of outer balloon 103 as show.

Figure 13:
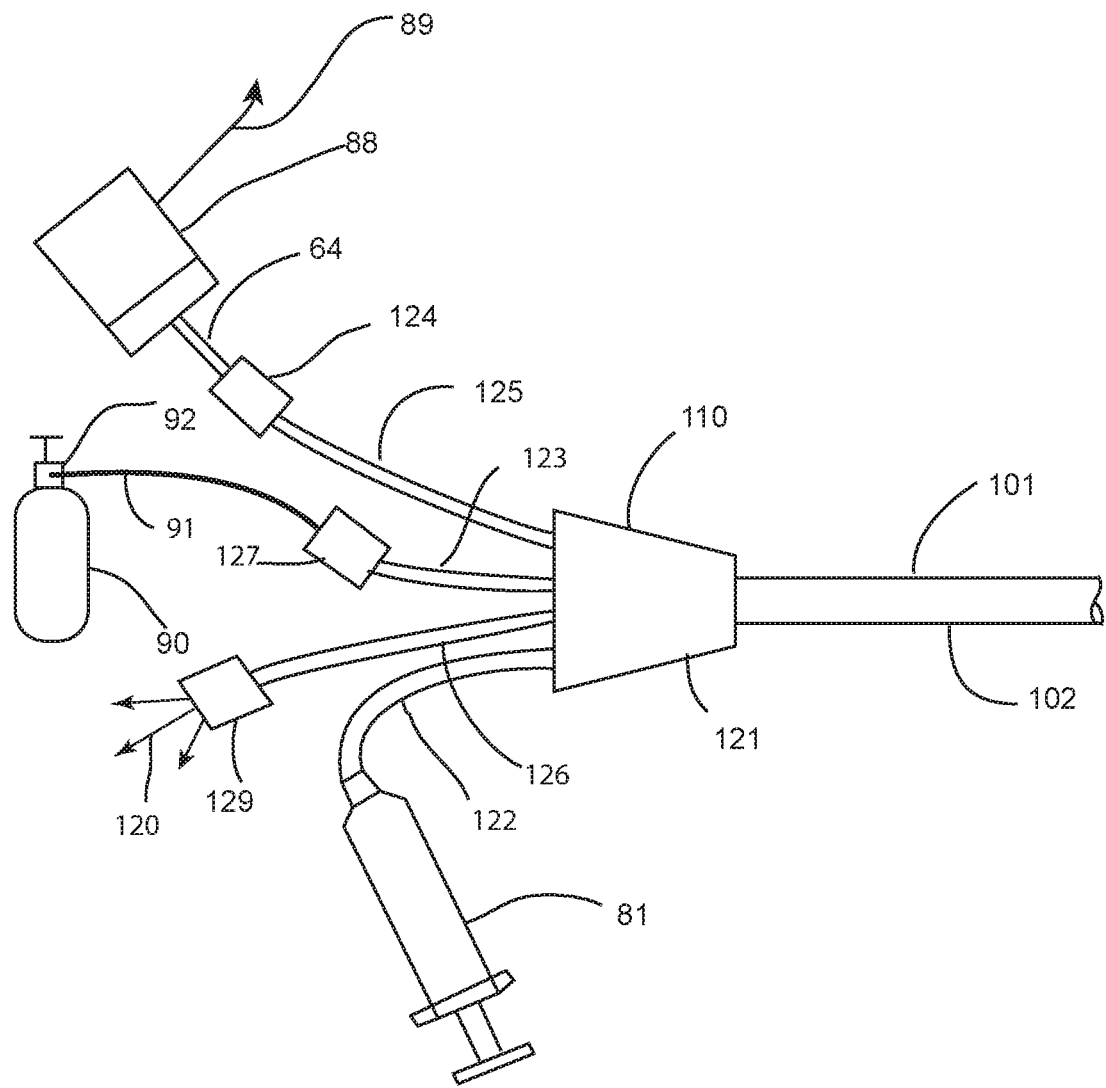
FIG. 13 shows a schematic illustration of the proximal terminal of the IGCB probe.

FIG. 13 is a schematic illustration of proximal terminal 110 of IGCB probe 101. Hub 121 fluidically connects outer balloon lumen 114 to outer balloon lumen hub tube 122, inner cryo balloon tube 107 to cryo balloon hub tube 123, and provides an insertion path for optical probe 64 into optical probe lumen 116 though optical probe port 86 and optical probe hub tube 125. Hub 121 is also configured to provide fluidic communication between inner cryo balloon lumen 117, inner cryo balloon vent tube 108, and inner thermal insulation balloon tube 109, and hub cryo exhaust tube 126. Hub 121 may be insert molded using mandrels to create discrete channels between the hub tubes and lumens described above. Those skilled in the art of surgical probe hub design and manufacture are familiar methods for designing and manufacturing the an IGCB probe hub as disclosed here within, therefore no further description is warranted. Imaging probe port 124 may comprise a Toughy Borst connector, or another type of surgical pressure port. Imaging module 88 comprises a camera and a light source, and has been previously described in detail. Inner cryo balloon tube 107 is connected to a source of liquid cryogen 90 by means of cryogen port 127, cryogen source hose 91, and cryogen connector 92. Liquid cryogen source 90 is depicted schematically as a cryogen tank. The liquid cryogen source may comprise a control console that controls the flow of cryogen based on user settings, and feedback from sensors, not shown. The liquid cryogen may be liquid carbon dioxide or liquid nitrogen, or a liquid chlorofluorocarbon compound. Alternatively, instead of using evaporative cooling, a Joules-Thompson effect (adiabatic gas expansion) cooling architecture could employed and still be within the scope of this invention. Nitrous oxide or argon gas would be the preferred cryogenic gasses for use if a Joule-Thompson cooling architecture is employed. Those skilled in the art cryosurgical probe design and manufacture are familiar the design attributes and trade-offs between liquid cryogen evaporative cooling and Joule-Thompson effect cooling architectures, and are familiar with the means for employing either cooling architecture within the scope of this invention, therefore no further discussion is warranted. Outer balloon lumen 114 is in fluidic communication with balloon lumen hub tube 122. Syringe 128 provides the user a means to either inflate outer balloon 103 prior to or after a cryosurgical step. Pressure relief valve 129 vents evaporated cryogen 120 to the ambient atmosphere while maintaining a set pressure within inner cryo balloon 105 and inner thermal insulation balloon 106 during liquid cryogen delivery. The pressure created by pressure relief valve 129 is used to maintain inflation of inner cryo balloon 105 and inner thermal insulation balloon 106 in order to maintain their conformity with the interior surface of outer balloon 103. Pressure relief valve 129 may have a fixed preset pressure relief setting, or pressure relief valve 129 may have a user adjustable pressure setting within a range of pressures that are lower than the burst strength of outer balloon 103. Pressure relief valve 129 may also comprise an audible indication of the volumetric flow rate of evaporated cryogen 120 exiting pressure relief valve 129. The audible indication may be in the form of a whistle where the pitch or volume of the whistle may increase as the flow rate of evaporated cryogen 120 increases. The audible signal may provide the user with an indication of tissue freezing effectiveness, or an indication of device failure, such as an inner cryo balloon 105 failure.

Figure 14:
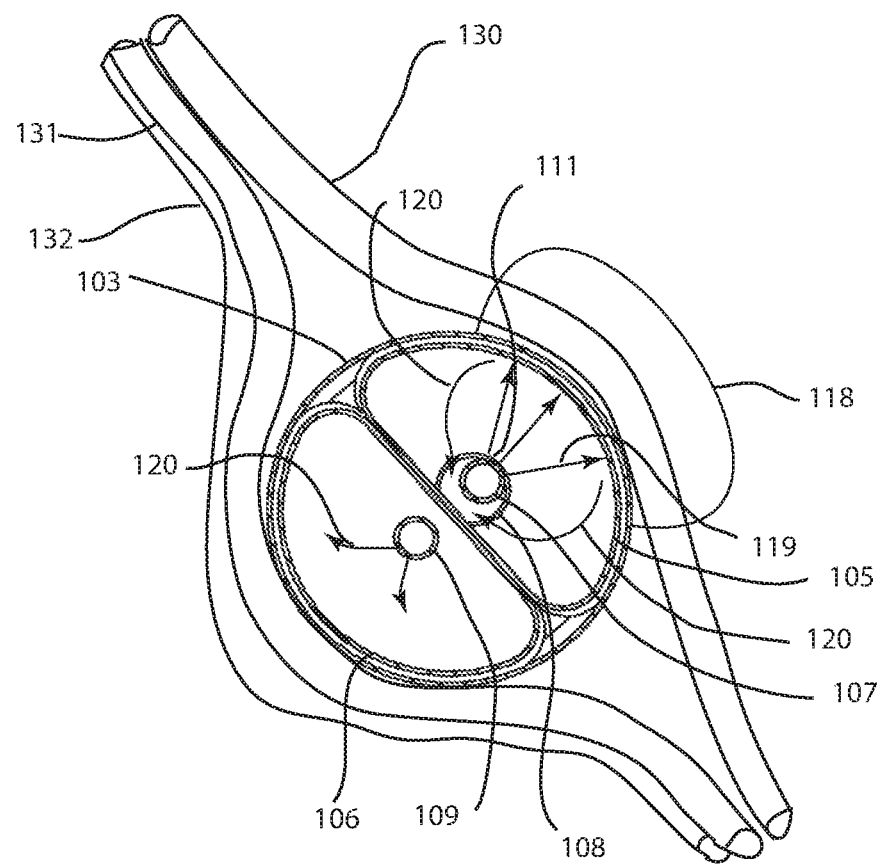
FIG. 14 shows a cross sectional end view of a nerve undergoing cryo-ablation using the IGCB probe.

FIG. 14 is cross sectional schematic illustration of a cryo-ablation of the function of nerve 130 using IGCB probe 101. As shown, IGCB probe 101 is positioned with balloon 103 inflated and separating nerve 130 from associated vein 131 and artery 132. Inner cryo balloon 105 is positioned adjacent to nerve 130. Liquid cryogen 119 is being sprayed against the inner wall of inner cryo balloon 105, resulting in ice ball 118 forming in adjacent tissue and encompassing nerve 130. Inner cryo balloon 105 and inner thermal insulation balloon 106 are inflated by evaporated cryogen gas 120 as previously described. Inner thermal insulation balloon 106 is adjacent to vein 131, and artery 132 providing protective thermal insulation from cryogenic injury.

The applications of the disclosed invention discussed above are not limited to certain treatments or regions of the body, but may include any number of other treatments and areas of the body. Modifications of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A cryosurgical probe, comprising:
   an elongated structure with a proximal end and a distal end;
   a cryo-ablation element disposed at the distal end of the elongated structure, wherein the cryo-ablation element includes an inflatable balloon structure and an insulation balloon, and the inflatable balloon structure includes a tissue freezing zone configured to cryogenically ablate a tissue region;
   an optical imaging device disposed within an interior of the inflatable balloon structure of the cryo-ablation element, wherein to position the tissue freezing zone at a tissue region, a wall of the inflatable balloon structure is configured to allow the optical imaging device to image the tissue region while the optical imaging device is disposed within the interior of the inflatable balloon structure; and
   a supply mechanism configured to introduce a cryogen into the inflatable balloon structure and to deliver the cryogen to the tissue freezing zone, wherein the insulation balloon limits cryo-ablation, via the tissue freezing zone, to the tissue region, while preventing cryo-ablation of another tissue region, wherein the insulation balloon is disposed within the inflatable balloon structure and configured to prevent cryo-ablation along a radial segment of the inflatable balloon structure.

2. The cryosurgical probe of claim 1, wherein the optical imaging device is disposed within the interior of the inflatable balloon structure when the supply mechanism introduces the cryogen into the inflatable balloon structure and delivers the cryogen to the tissue freezing zone.

3. The cryosurgical probe of claim 1, wherein the inflatable balloon structure comprises an optical imaging window, and the optical imaging device images the tissue region through the optical imaging window.

4. The cryosurgical probe of claim 1, wherein the inflatable balloon structure is configured to dilate tissue surrounding the tissue region prior to the supply mechanism introducing the cryogen into the inflatable balloon structure and delivering the cryogen to the tissue freezing zone.

5. The cryosurgical probe of claim 1, wherein the supply mechanism is configured to introduce a liquid cryogen into the inflatable balloon structure from a cryogenic fluid source fluidly coupled to the inflatable balloon structure such that the inflatable balloon structure is inflated from a deflated configuration to an expanded configuration while the optical imaging device is positioned within the inflatable balloon structure.

6. The cryosurgical probe of claim 5, wherein the supply mechanism introduces the liquid cryogen into the inflatable balloon structure by spraying the liquid cryogen from an array of cryogen nozzles towards an inner wall of the inflatable balloon structure corresponding to the tissue freezing zone so as to evaporate the liquid cryogen in the inflatable balloon structure, and
   wherein the inflatable balloon structure is inflated as a result of evaporation of the liquid cryogen within the interior of the inflatable balloon structure.

7. The cryosurgical probe of claim 6, wherein the inflatable balloon structure is configured to be deflated by venting the evaporated liquid refrigerant from the inflatable balloon structure using a second lumen.

8. The cryosurgical probe of claim 7, wherein the elongated structure includes a first lumen and the second lumen extending in the elongated structure between the proximal end and the distal end of the elongated structure,
   wherein introducing the liquid refrigerant into the inflatable balloon structure comprises supplying the liquid refrigerant to the inflatable balloon structure using the first lumen, and
   wherein deflating the inflatable balloon structure comprises venting the evaporated liquid refrigerant from the inflatable balloon structure using the second lumen.

9. The cryosurgical probe of claim 8, wherein the first lumen and the second lumen are coaxial with each other.

10. The cryosurgical probe of claim 1, wherein the optical imaging device is configured to rotate around a longitudinal axis of the cryo-ablation element while positioned within the cryo-ablation element.

11. The cryosurgical probe of claim 1, wherein the optical imaging device is configured to translate along a longitudinal axis of the cryo-ablation element while positioned within the cryo-ablation element.

12. The cryosurgical probe of claim 1, wherein the optical imaging device comprises an imaging element coupled to a fiber bundle, the fiber bundle coupled to an imaging module including a camera or a video display at the proximal end of the elongated structure.

13. The cryosurgical probe of claim 12, wherein the fiber bundle comprises an optical fiber bundle coupled to the camera and an illuminating fiber bundle coupled to a light source of the imaging module and configured to illuminate a field of vision of the imaging element.

14. The cryosurgical probe of claim 13, wherein the optical fiber bundle comprises a central coherent fiber bundle and the illuminating fiber bundle comprises an outer non-coherent fiber bundle.

15. The cryosurgical probe of claim 1, wherein the cryo-ablation element has a longitudinal axis extending between ends of the cryo-ablation element, and the optical imaging device has a field of view that is in a lateral direction that is transverse to the longitudinal axis.

16. The cryosurgical probe of claim 15, wherein the optical imaging device comprises a reflective surface that directs light received from the lateral direction to a direction parallel to the longitudinal axis.

17. The cryosurgical probe of claim 1, wherein the optical imaging device is configured to be withdrawn out of the cryo-ablation element.

18. The cryosurgical probe of claim 1, wherein the cryo-ablation element further includes an inner cryo balloon disposed with the insulation balloon in the inflatable balloon structure, wherein the inner cryo balloon is configured to receive the cryogen to produce the tissue freezing zone.

19. The cryosurgical probe of claim 18, wherein the inner cryo balloon and the insulation balloon are configured to be inflated and conform to an inner surface of the inflatable balloon structure.

* * * * *